United States Patent [19]
Cheng et al.

[11] Patent Number: 5,674,898
[45] Date of Patent: Oct. 7, 1997

[54] METHODS AND THERAPEUTIC COMPOSITIONS FOR TREATING CYSTIC FIBROSIS

[75] Inventors: Seng Hing Cheng, Wellesley; Shaona Lee Fang, Sudbury; Henry Hoppe, IV, Acton; Alan Edward Smith, Dover, all of Mass.

[73] Assignee: Genzyme Corporation, Cambridge, Mass.

[21] Appl. No.: 72,708

[22] Filed: Jun. 7, 1993

Related U.S. Application Data

[63] Continuation-in-part of Ser. No. 935,603, Aug. 26, 1992, abandoned, which is a continuation-in-part of Ser. No. 613,592, Nov. 15, 1990, abandoned, and a division of Ser. No. 589,295, Sep. 27, 1990, abandoned, which is a continuation-in-part of Ser. No. 488,307, Mar. 5, 1990, abandoned.

[51] Int. Cl.$^6$ .................. C07C 53/126; C07C 53/125; C07C 53/122; A61K 31/19
[52] U.S. Cl. .................. 514/557; 514/546; 514/549; 514/552; 514/548; 514/560; 514/826; 514/851; 560/205; 560/265; 562/598; 562/606
[58] Field of Search .................. 560/205, 265; 562/598, 606; 514/546, 549, 552, 557, 558, 560, 826, 851

[56] References Cited

U.S. PATENT DOCUMENTS

| | | | |
|---|---|---|---|
| 4,873,316 | 10/1989 | Meade et al. | 530/412 |
| 5,240,846 | 8/1993 | Collins et al. | 435/240.1 |

FOREIGN PATENT DOCUMENTS

| | | |
|---|---|---|
| 0446017A1 | 9/1991 | European Pat. Off. |
| WO91/02796 | 8/1990 | WIPO |
| WO91/10734 | 1/1991 | WIPO |

OTHER PUBLICATIONS

Annunziato et al., "Treatment with Sodium Butyrate." Chromasoma (Berl) 1988 96: 132–138.
McKnight et al. "Butyrate and Related Inhibition of Histone, etc." Cell, vol. 22, 469–477, 1980.
Cheng et al., "Functional Activation, etc." Am. J. Physiology 12(4) 1995 pp. L615–L624.
Boggaram et al., "Regulation of Expression, etc." J. Biol. Chem., vol. 264, No. 19, pp. 11421–11427 (1989).
Bates et al. "Modulation of P–Glycoprotein Phosphorylation, etc." Biochemistry 1992, 31, 6366–6372.
Perrine et al. "Sodium Butyrate Enhances Fetal Globin Gene Expression, etc." Blood, vol. 74, No. 1 (Jul.), 1989: pp. 454–459.
Perrine et al., "Butyric Acid Analogues, etc." Biochemical and Biophysical Research Communication, vol. 148, No. 2, pp. 694–700 (1987).
Novogrodsky et al. "Effect of Polar Organic Compounds on Leukemic Cells" Cancer 51:9–14 (1983).
Nichols et al. "Regulation of Surfactant Protein A, etc" Am. J. Phys. 259, 1448–1495, (1990).

Toscani et al. "Sodium Butyrate in Combination with Insulin, etc." The Journal of Biological Chemistry vol. 265, No. 10, pp. 5722–5730, (1990).
Saito et al., "Flow Cytometric and Biochemical Analysis, etc." Cytometry, 12: 757–764 (1991).
Prasad et al. "Mini Review: Butyric Acid, etc." Life Sciences, vol. 27, pp. 1351–1358 (1980).
Peterec, et al. "Butyrate Modulates Surfactant Protein, etc." Am. J. Physiol. 267 (Lung. Cell. Mol. Physiol. 11):L9–L15, (1994).
Annunziato, A.T. et al., "Treatment with Sodium Butyrate Inhibits the Complete Condensation of Interphase Chromatin", Chromosoma, 96:132–138 (1988).
Bates, S.E. et al., "Modulation of P–Glycoprotein Phosphorylation and Drug Transport by Sodium Butyrate", Biochemistry, 31:6366–6372 (1992).
Boggaram, V. et al., "Regulation of Expression of the Gene Encoding the Major Surfactant Protein (SP-A) in Human Fetal Lung in Vitro", The Journal of Biological Chemistry, 264:11421–11427 (1989).
Cheng, S.A. et al., "Functional Activation of the Cystic Fibrosis Trafficking Mutant ΔF508–CFTR By Overexpression", American Journal of Physiology, 12: L615–L624 (1995).
McKnight, G.S. et al., "Butyrate and Related Inhibitors of Histone Deacetylation Block the Induction of Egg White Genes by Steroid Hormones", Cell, 22: 469–477 (1980).
Nichols, K.V. et al., "Regulation of Surfactant Protein A mRNA By Hormones and Butyrate in Cultured Fetal Rat Lung", American Journal of Physiology, 259:L448–L495 (1990).
Nichols, K.V. et al., "Inhibition of SP–A mRNA By Butyric Acid Analogs In Fetal Rat Lung Explants", Pediatric Research, 27: 49A (1990).
Novogrodsky, A. et al., "Effect of Polar Organic Compounds on Leukemic Cells", Cancer, 51: 9–14 (1983).
Perrine, S.P. et al., "Butyric Acid Analogues Augment γ Globin Gene Expression in Neonatal Erythroid Progenitors", Biochemical and Biophysical Research Communications, 148: 694–700 (1987).
Perrine, S.P. et al., "Sodium Butyrate Enhances Fetal Globin Gene Expression in Erythroid Progenitors of Patients With HbSS and β Thalassemia", Blood, 74:454–459 (1989).
Peterec, S.M. et al., "Butyrate ModulatesSurfactant Protein mRNA in Fetal Rat Lung By Altering mRNA Transcription and Stability", American Journal of Physiology, 11: L9–L15 (1994).
Prasad, K.N., "Butyric Acid: A Small Fatty Acid With Diverse Biological Functions", Life Sciences, 27: 1351–1358 (1980).

(List continued on next page.)

Primary Examiner—Peter O'Sullivan

[57] ABSTRACT

Methods and compositions for treating Cystic Fibrosis by mobilizing mutant forms of CFTR, which retain at least some functional activity, to the plasma membrane where they can mediate chloride ion transport are disclosed.

34 Claims, 17 Drawing Sheets

OTHER PUBLICATIONS

Saito, S.et al., "Flow Cytometric and Biochemical Analysis of Dose–Dependent Effects of Sodium Butyrate on Human Endometrial Adenocarcinoma Cells", *Cytometry*, 12:757–764 (1991).

Toscani, A. et al., "Sodium Butyrate in Combination With Insulin or Dexamethasone Can Terminally Differentiate Actively Proliferating Swiss 3T3 Cells Into Adipocytes" *The Journal of Biological Chemistry*, 265: 5722–5730 (1990).

Drumm, M.L. et al. (1991) "Chloride Conductance Expressed by ΔF508 and Other Mutant CFTRs in Xenopus Oocytes" *Science* 254: 1797–1799.

Machamer, C.E. (1988) "Vesicular Stomatitis Virus G Proteins With Altered Glycosylation Sites Display Temperature–Sensitive Intracellular Transport and are Subject To Abberant Intermolecular Disulfide Bonding" *J. Biol. Chem.* 263:5955–5960;.

J. Marshall et al., "Stoichiometry of Recombinant Cystic Fibrosis Transmembrane Conductance Regulator in Epithelial Cells and Its Functional Reconstitution into Cells in vitro", *The Journal of Biological Chemistry*, 269, 1994, pp. 2987–2995.

J. Amara et al., "Intracellular protein trafficking defects in human disease", *Trends in Cell Biology*, 2, 1992, pp. 145–149.

C. Li et al., "The cystic fibrosis mutation (ΔF508) does not influence the chloride channel activity of CFTR", *Nature Genetics*, 3, 1993, pp. 311–316.

W. Dalemans et al., "Altered chloride ion channel kinetics associated with the ΔF508 cystic fibrosis mutation", *Nature*, 354, 1991, pp. 526–528.

M. Drumm et al., "Chloride Conductance Expressed by ΔF508 and Other Mutant CFTRs in *xenopus* Oocytes", *Science*, 254, 1991, pp. 1797–1799.

C.Machamer et al., "Vesicular Stomatitis Virus G Proteins with Altered Glycosylation Sites Display Temperature–sensitive Intracellular Transport and Are Subject to Aberrant Intermolecular Disulfide Bonding", *The Journal of Biological Chemistry*, 263, 1988, pp. 5955–5960.

Andrews, G.K. et al. (1987) "Butyrate Selectively Activates the Metallothionein Gene in Teratocarcinoma Cells and Induces Hypersensitivity to Metal Induction" *Nucleic Acids Res.* 15(13):5461–5475.

Rommens, J.H. et al. (1989) "Identification of the Cystic Fibrosis Gene: Chromosome Walking and Jumping" *Science* 245: 1059–1065.

Kerem, B.S. et al. (1989) "Identification of the Cystic Fibrosis Gene: Genetic Analysis" *Science* 245:1073–1080.

Dorin, J.R. et al. (1987) "A Clue to the Basic Defect in Cystic Fibrosis from Cloning the CF Antigen Gene" *Nature* 326:614–617;.

Kerem, B–S. et al. (1990) "Identification of Mutations in Regions Corresponding to the Two Putative Nucleotide (ATP)–Binding Folds of the Cystic Fibrosis Gene" *Proc. Natl. Acad. Sci.* 87:8447–8451;.

Cheng. S. H. et al. (1990) "Defective Intracellular Transport and Processing of CFTR is the Molecular Basis of Most Cystic Fibrosis" *Cell* 63:827–834;.

Riordan, J.R. et al. (1989) "Identification of the Cystic Fibrosis Gene: Cloning and Characterization of Complementary DNA" *Science* 245:1066–1073;.

Drumm, M.L. et al. (1990) "Correction of the Cystic Fibrosis Defect In Vitro By Retrovirus–Mediated Gene Transfer" *Cell* 62:1227–1233;.

Gregory, R.J. et al. (1990) "Expression and Characterization of the Cystic Fibrosis Transmembrane Conductance Regulator" *Nature* 347:382–386;.

Rich, D.P. et al. (1990) "Expression of the Cystic Fibrosis Transmembrane Conductance Regulator Corrects Defective Chloride Channel Regulation in Cystic Fibrosis Airway Epithelial Cells" *Nature* 347:358–363;.

Dalemans, W. et al. (1991) "Altered Chloride Ion Channel Kinetics Associated with the ΔF508 Cystic Fibrosis Mutation" *Nature* 354:526–528;.

Dean, M. et al. (1990) "Multiple Mutations in Highly Conserved Residues Are Found in Mildly Affected Cystic Fibrosis Patients" *Cell* 61:863–870;.

Cutting, G.R. et al. (1990) "A Cluster of Cystic Fibrosis Mutations in the First Nucleotide–Binding Fold of the Cystic Fibrosis Conductance Regulator Protein" *Nature* 346:366–369;.

Cheng, S. H. et al. (1991) "Phosphorylation of the R Domain by cAMP–Dependent Protein Kinase Regulates the CFTR Chloride Channel" *Cell* 66:1027–1036;.

Anderson, M.P. et al. (1991) "Nucleoside Triphosphates are Required to Open the CFTR Chloride Channel" *Cell* 67:775–784;.

Hamosh, A. et al. (1991) "Severe Deficiency of Cystic Fibrosis Transmembrane Conductance Regulator Messenger RNA Carrying Nonsense Mutations R553X and W1316X in Respiratory Epithelial Cells of Patients with Cystic Fibrosis" *J. Clin. Invest.* 88: 1880–1885;.

Rich, D.P. et al. (1991) "Effect of Deleting the R Domain on CFTR–Generated Chloride Channels" *Science* 253:205–207;.

Gregory, R.J. et al. (1991) "Maturation and Function of Cystic Fibrosis Transmembrane Conductance Regulator Variants Bearing Mutations in Putative Nucleotide–Binding Domains 1 and 2" *Mol. Cell. Biology* 8(11):3886–3893;.

Dork, T. et al. (1991) "Cystic Fibrosis with Three Mutations in the Cystic Fibrosis Transmembrane Conductance Regulator Gene" *Human Genetics* 87:441–446;.

Anderson, M.P. et al. (1991) "Generation of cAMP–Activated Chloride Currents by Expression of CFTR" *Science* 251:679–682;.

Kartner, N. et al. (1991) "Expression of the Cystic Fibrosis Gene in Non–Epithelial Invertabrate Cells Produces a Regulated Anion Conductance" *Cell* 64:681–691;.

Anderson, M.P. et al. (1991) "Demonstration That CFTR Is a Chloride Channel by Alteration of Its Anion Selectivity" *Science* 253:202–205;.

Tsui, L–C. (1992) "The Spectrum of Cystic Fibrosis Mutations" *Trends in Genetics* 8(11):392–398;.

Denning, G.M. et al. (1992) "Abnormal Localization of Cystic Fibrosis Transmembrane Conductance Regulator in Primary Cultures of Cystic Fibrosis Airway Epithelia" *J. Cell Biol.* 118(3):551–559;.

Smith, A.E. (1992) "Emerging Therapies for Cystic Fibrosis" Section V–Topics in Biology *in Ann. Rep. Med. Chem.* 27:235–243;.

Welsh, M.J. (1992) "Cystic Fibrosis Transmembrane Conductance Regulator: A Chloride Channel with Novel Regulation" *Neuron* 8:821–829;.

Kartner, N. et al. (1992) "Mislocalization of ΔF508 CFTR in Cystic Fibrosis Sweat Gland" *Nature Genetics* 1:321–327;.

Denning, G.M. et al (1992) "Processing of Mutant Cystic Fibrosis Transmembrane Conductance Regulator is Temperature–Sensitive" *Nature* 358:761–764;.

DiTullo, P. et al (1992) "Production of Cystic Fibrosis Transmembrane Conductance Regulator in the Milk of Transgenic Mice" *Bio/Technology* 10:74–77;.

Rosenfeld, M.A. et al. (1992) "In Vivo Transfer of the Human Cystic Fibrosis Transmembrane Conductance Regulator Gene to the Airway Epithelium" *Cell* 68:143–155;.

Thomas, P.J. et al. (1992) "The Cystic Fibrosis Transmembrane Conductance" *J. Biol. Chem* 267(9):5727–5730;.

Cheng, S.H. et al (1993) "Defective Intracellular Processing of CFTR as the Molecular Basis of Cystic Fibrosis" *Cystic–Fibrosis Current Topics:* vol. 1:175–189;.

Teem, J.L. et al. (1993) "Identification of Revertants for the Cystic Fibrosis ΔF508 Mutation Using STE6–CFTR Chimeras in yeast" *Cell* 73:335–346;.

Welsh, M.J. and Smith, A.E. (1993) "Molecular Mechanisms of CFTR Chloride Channel Dysfunction in Cystic Fibrosis" *Cell* 73:1251–1254;.

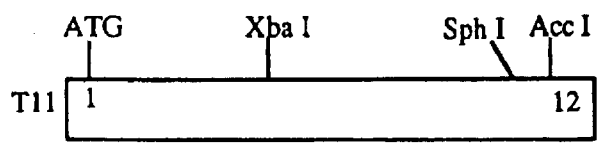
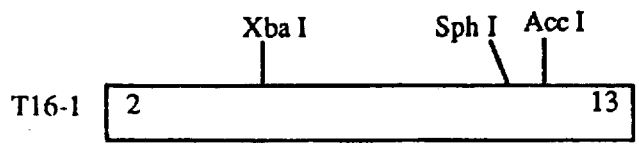
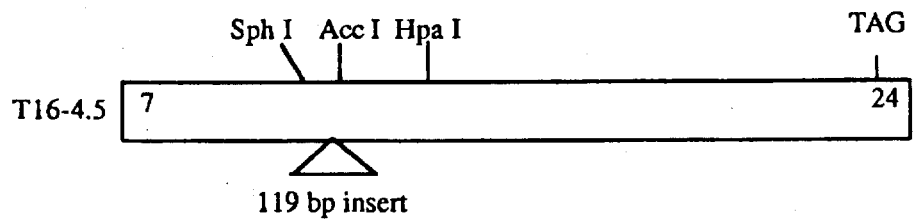
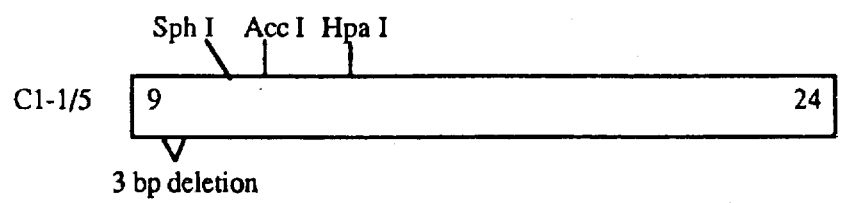
FIG. 1

```
                      bp 1716                                     ====Synthetic Intron====
                         |                                    |------1195RG------------------------
   s                     |                                    |
   p                     |                                    |
   h                     |                                    |
   I                     |
|------CCAACTAGAAGAGGTAAGGGCTCACCAGTTCAAAATCTGAAGTGGAGACAGGAC
       GTACGGTTGATCTTCTCCATTCCCGAGTGGTCAAGTTTAGACTTCACCTCTGTCCTG
                                   <-----------1198RG---------|
                                                              |
                                                              ============================
                                                                                           bp 1717
                                                                                              |
                                                                                              |
       CTGAGGTGACAATGACATCTACTCTGACATTCTCCTCAGGACATTCCAAGTTTGCAG              H
       GACTCCACTGTTACTGTAGATGAGACTGTAAGAGGAGTCCTGTAGAGGTTCAAACGTC              i
                                     |----------1197RG-----------              n
                            --|>|---                                           c
                              |<|---                                           I
                                                                               I
       |----------1196RG----------------------------------------------->
       AGAAAGACAATATAGTTCTTGGAGAAGGTGGAATCACACTGAGTGGAGGTC
       TCTTTCTGTTATATCAAGAACCTCTTCCACCTTAGTGTGACTCACCTCCAG
|------
```

FIG. 6

METHODS AND THERAPEUTIC COMPOSITIONS FOR TREATING CYSTIC FIBROSIS

RELATED APPLICATIONS

This application is a continuation-in-part application of U.S. Ser. No. 07/935,603 filed Aug. 26, 1992; now abandoned, which is a continuation-in-part application of U.S. Ser. No. 07/613,592, now abandoned filed Nov. 15, 1990, and a divisional application of U.S. Ser. No. 07/589,295, now abandoned filed Sep. 27, 1990, which is a continuation-in-part application of U.S. Ser. No. 7/488,307, now abandoned, filed Mar. 5, 1990. This application is also related to the subject matter described in application U.S. Ser. No. 07/985,478, now abandoned filed Dec. 2, 1992. All of the above patent applications are incorporated herein by reference.

BACKGROUND OF THE INVENTION

Cystic Fibrosis (CF) is the most common fatal genetic disease in humans (Boat et al., 1989). Based on both genetic and molecular analysis, a gene associated with CF was isolated as part of 21 individual cDNA clones and its protein product predicted (Kerem et al., 1989; Riordan et al., 1989; Rommens et al., 1989).

U.S. Ser. No. 488,307 describes the construction of the gene into a continuous strand, expression of the gene as a functional protein and confirmation that mutations of the gene are responsible for CF. (See also Gregory et al., 1990; Rich et al., 1990). The copending patent application also discloses experiments which showed that proteins expressed from wild type but not a mutant version of the cDNA complemented the defect in the cAMP regulated chloride channel shown previously to be characteristic of CF.

The protein product of the CF associated gene is called the cystic fibrosis transmembrane conductance regulator (CFTR) (Riordan et al., 1989). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) P-glycoprotein, bovine adenyl cyclase, the yeast STE6 protein as well as several bacterial amino acid transport proteins (Riordan et al., 1989; Hyde et al., 1990). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan et al., 1989; Welsh, 1986; Frizzel et al., 1986; Welsh and Liedtke, 1986; Schoumacher et al., 1987; Li et al., 1988; Hwang et al., 1989; Li et al., 1989).

Sequence analysis of the CFTR gene of CF chromosomes has revealed a variety of mutations (Cutting et al., 1990; White et al., 1990; Dean et al., 1990; and Kerem et al., 1989 and 1990). Population studies have indicated that the most common CF mutation, a deletion of the 3 nucleotides that encode phenylalanine at position 508 of the CFTR amino acid sequence ($\Delta$F508), is associated with approximately 70% of the cases of cystic fibrosis. This mutation results in the failure of an epithelial cell chloride channel to respond to cAMP (Frizzel et al., 1986; Welsh, 1986; Li et al., 1988; Quinton, 1989). In airway cells, this leads to an imbalance in ion and fluid transport. It is widely believed that this causes abnormal mucus secretion, and ultimately results in pulmonary infection and epithelial cell damage.

Studies on the biosynthesis (Cheng et al., Cell 63:827–834(1990); Gregory et al., Mol.Cell Biol. 11:3886–3893 (1991)) and localization (Denning et al., J. Cell Biol. 118:551–559 (1992)) of CFTR $\Delta$F508, as well as other CFTR mutants, indicate that many CFTR mutant proteins are not processed correctly and, as a result, are not delivered to the plasma membrane (Gregory et al., Mol.Cell-.Biol. 11: 3886–3893 (1991)). These conclusions are consistent with earlier functional studies which failed to detect cAMP stimulated Cl– channels in cells expressing CFTR $\Delta$F508 (Rich et al., i Nature 347:358–363 (1990); Anderson et al., Science 251:679–682 (1991)).

A method for delivering mutant CFTR proteins, which retain at least some functional activity, to the plasma membrane of epithelial cells where they can mediate chloride ion transport would be a useful therapy for cystic fibrosis.

SUMMARY OF THE INVENTION

The invention described herein relates to methods and compositions useful for delivering mutant cystic fibrosis transmembrane regulator (CFTR) proteins, which retain at least some functional activity, to the plasma membrane of epithelial cells, where they can mediate chloride ion transport.

In one aspect, the invention features a method for mobilizing a mutant CFTR in a cell comprising exposing the cell to a temperature below normal body temperature (i.e., below 37° C.) for a period of time sufficient to alter the subcellular distribution of the mutant protein. In preferred embodiments, the cell is lung epithelia and the temperature is in the range of 20°–30° C.

In another aspect, the invention features a method for treating cystic fibrosis in a patient having a mutant CFTR, which retains at least some functional activity, comprising exposing the patient's lung epithelia to a temperature below normal body temperature for a period of time sufficient to mobilize the mutant CFTR to the plasma membrane of the lung epithelia, where the mutant CFTR can mediate chloride ion transport. In a preferred embodiment, the method comprises having the patient inhale air of a temperature below 37° C. for an appropriate period of time. In another preferred embodiment, the method comprises implanting in the patient's lung, a non-toxic, non-immunogenic agent which lowers the temperature in the vicinity of the lung so that it is below normal body temperature.

In a further aspect, the invention features a non-toxic, non-immunogenic agent, which is capable of being implanted in a patient's lung and of reducing the temperature in the vicinity of the lung so that it is below normal body temperature.

The present invention also pertains to a method for treating a subject having cystic fibrosis (CF). The method involves the administration of an effective amount of a protein enhancing agent to the subject having CF. The protein enhancing agent increases the intracellular level of at least one cellular protein in a CF-associated cell such that a mutant CFTR protein generates functional chloride channels in the cells of the subject.

The present invention further pertains to a method for treating a subject's lung epithelia containing a mutant CFTR protein. The method involves contacting a subject's lung epithelia with a protein enhancing agent which increases the level of at least one cellular protein such that a mutant CFTR protein present in the lung epithelia mediates chloride ion transport across the cell membrane.

The present invention even further pertains to a method for treating a subject having CF by administering an effective amount of a differentiating agent or a carboxy-compound to the subject. The mutant CFTR present in CF-associated cells of the subject generates functional chloride channels or mediates chloride in a transport after treatment with the differentiating agent or carboxy-compound.

Other aspects of the present invention include therapeutic compositions and packaged drugs for treating subjects having CF. The therapeutic compositions include a therapeutically effective amount of at least one of the forementioned agents, (protein enhancing agent, differentiating agent or carboxy-compound) and a pharmaceutically acceptable carrier. The packaged drug includes at least one of the forementioned agents and instructions for administrating the agent for treating subjects having CF.

The above discussed and many other features and advantages of the present invention will become better understood by reference to the following detailed description when taken in conjunction with the accompanying drawings.

BRIEF DESCRIPTION OF THE TABLES AND DRAWINGS

Further understanding of the invention may be had by reference to the tables and figures wherein:

Table 1 shows the sequence of that portion of CFTR cDNA encoding the complete CFTR protein within plasmid pSC-CFTR2 including the amino acid sequence of the CFTR open reading frame;

Table 2 shows CFTR mutants wherein the known association with CF (Y, yes or N, no), exon localization, domain location and presence (+) or absence (−) of bands A, B and C of mutant CFTR species is shown. TM6, indicates transmembrane domain 6; NBD nucleotide binding domain: ECD, extracellular domain and Term, termination at 21 codons past residue 1337.

The convention for naming mutants is first the amino acid normally found at the particular residue, the residue number (Riordan et al., 1989) and the amino acid to which the residue was converted. The single letter amino acid code is used: D, aspartic acid; F, Phenylalanine; G, glycine; I, isoleucine; K, lysine; M, methionine; N, asparagine; Q, glutamine; R, arginine; S, serine; W, tryptophan. Thus G551D is a mutant in which glycine 551 is converted to aspartic acid;

FIG. 1 shows alignment of CFTR partial cDNA clones used in construction of cDNA containing complete coding sequence of the CFTR, only restriction sites relevant to the DNA constructions described below are shown.0

FIG. 6 shows the DNA sequence of synthetic DNAs used for insertion of an intron into the CFTR cDNA sequence, with the relevant restriction endonuclease sites and nucleotide positions noted.

FIGS. 12A, 12B, 12C, and 12D show immunolocalization of wild type and ΔF508 mutant CFTR; and COS-7 cells transfected with pMT-CFTR or pMT-CFTR-ΔF508.

Figure 13:
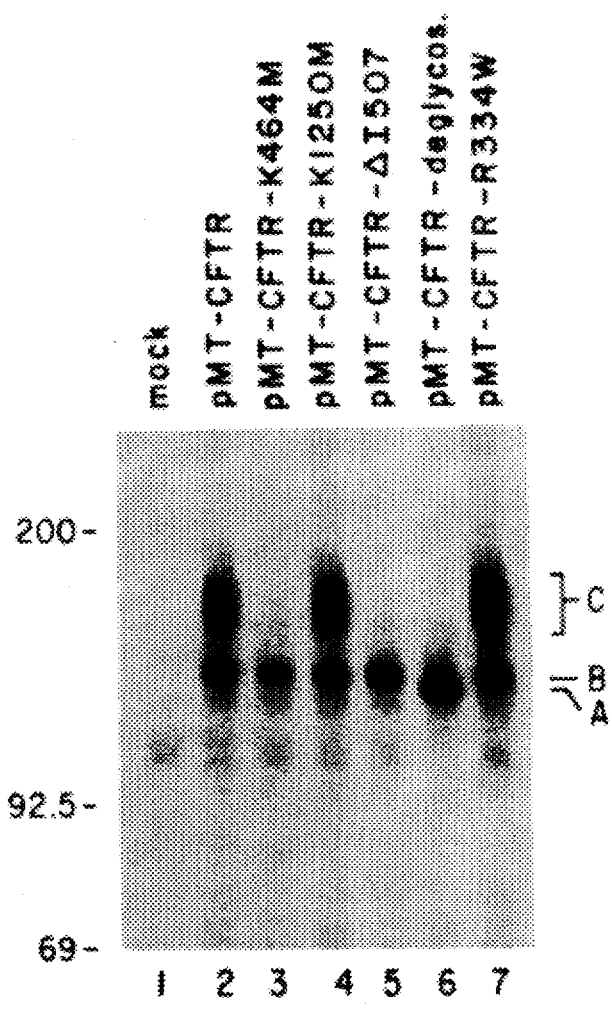

FIG. 13 shows an analysis of mutant forms of CFTR.

Figure 14:
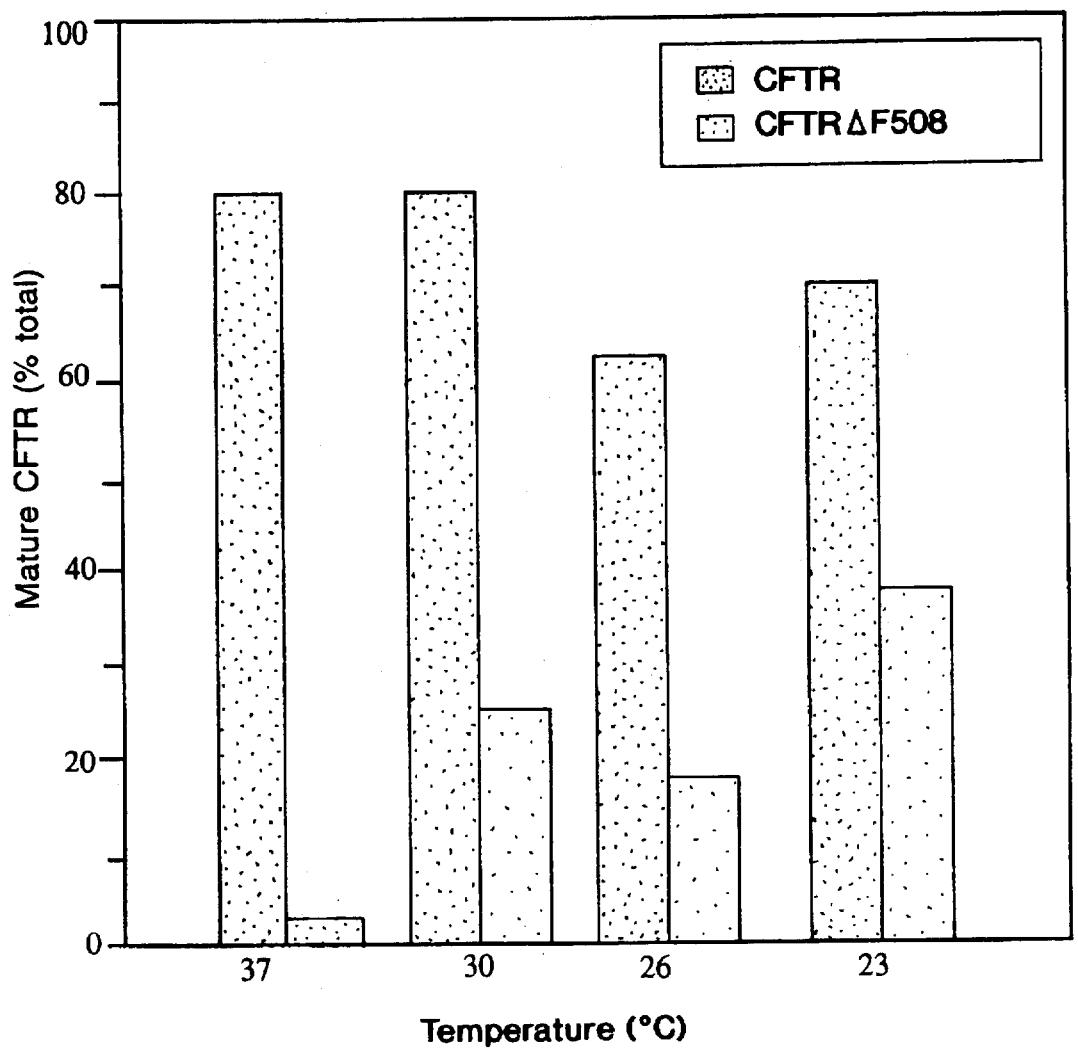

FIG. 14 is a graph showing the effect of temperature on the processing of CFTR ΔF508 and wild type CFTR.

Figure 15:
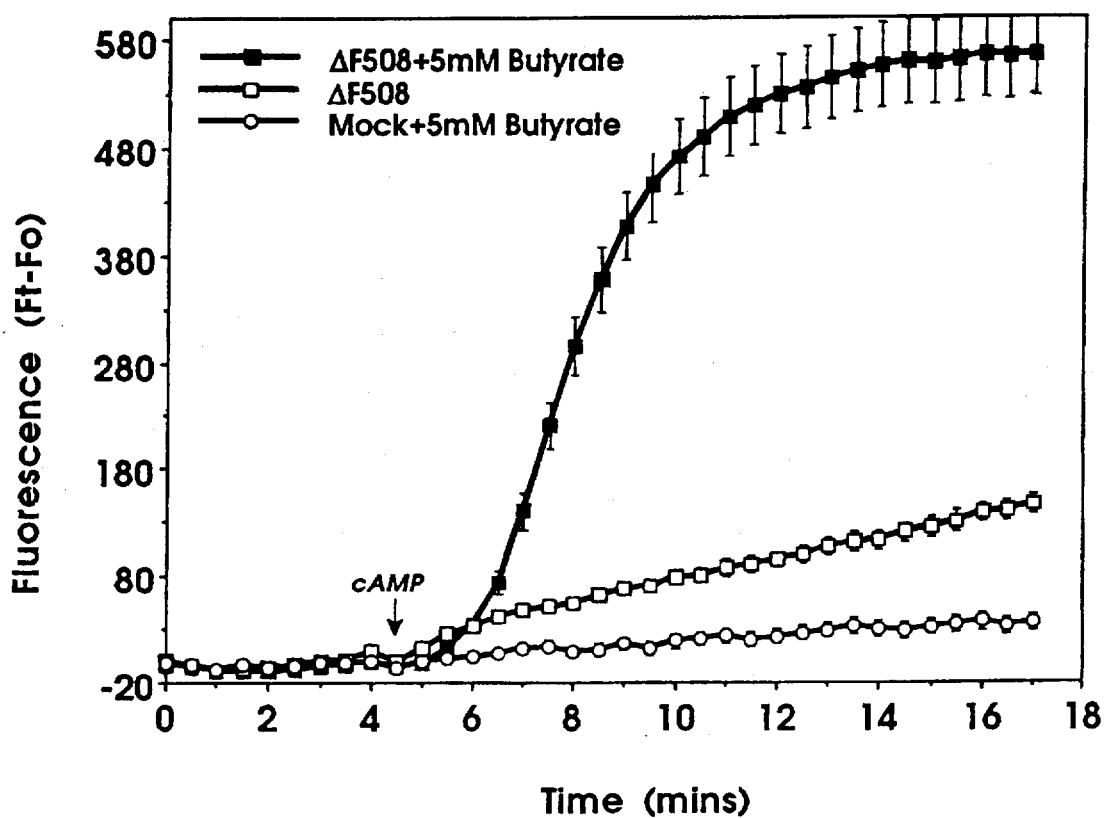

FIG. 15 is a graph depicting the effect of butyrate on recombinant C127-ΔF508 cells.

Figure 16:
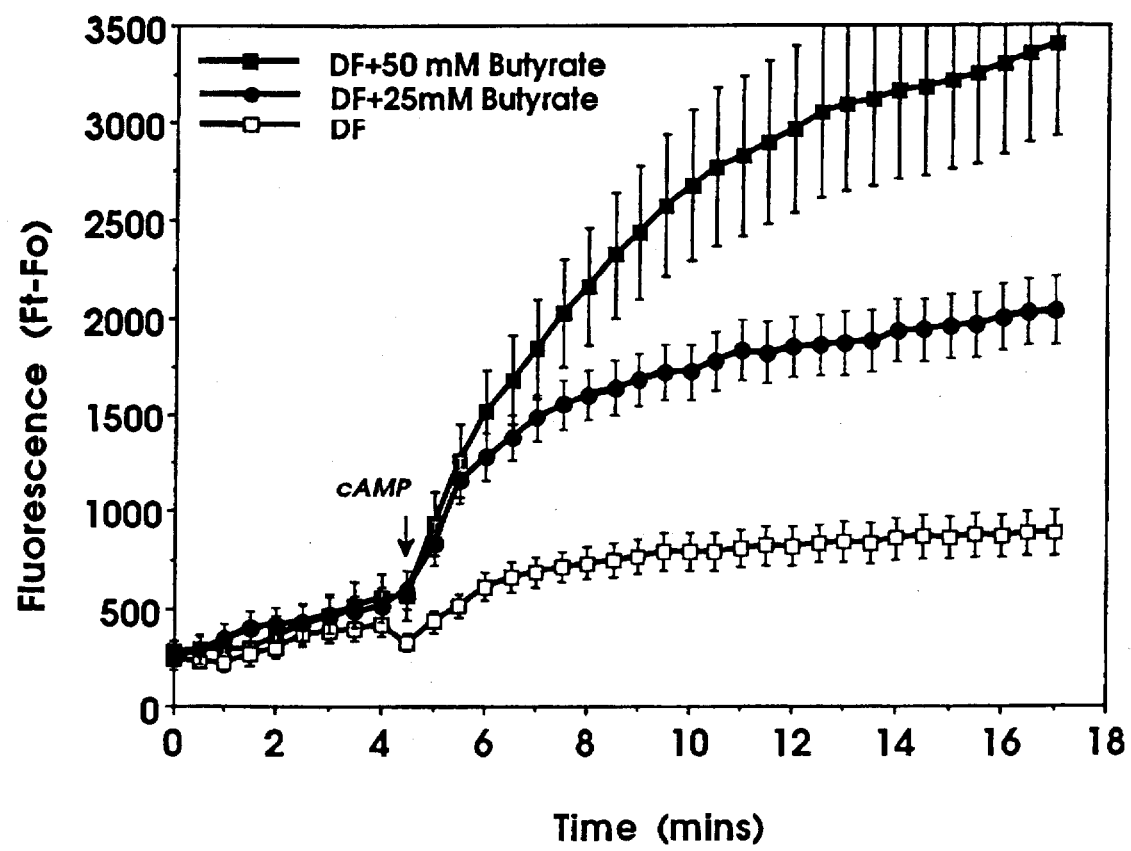

FIG. 16 is a graph depicting the effect of butyrate on ΔF508 airway epithelial cells.

DETAILED DESCRIPTION AND BEST MODE

Definitions

The term "intron" identifies an intervening sequence within a gene for the gene product that does not constitute protein coding sequences. In eukaryotic cells introns are removed from the primary RNA transcript to produce the mature mRNA.

The term "splice" refers to the removal of an intron from the primary RNA transcript of a gene.

The term "polylinker" refers a closely arranged series of synthetic restriction enzyme cleavage sites within a plasmid.

The term "open reading frame" refers to a nucleotide sequence with the potential for encoding a protein.

The term "agarose gel purification" refers to the separation of DNA restriction fragments by electrophoresis through an agarose gel followed by purification of the desired DNA fragments from the agarose gel as described below in general methods.

The term "maintained" refers to the stable presence of a plasmid within a transformed host cell wherein the plasmid is present as an autonomously replicating body or as an integrated portion of the host genome.

The term "cell culture" refers to the containment of growing cells derived from either a multicellular plant or animal which allows the cells to remain viable outside of the original plant or animal.

The term "host cell" refers to a microorganism including yeast, bacteria, insect and mammalian cells which can be grown in cell culture and transfected or transformed with a plasmid or vector encoding a molecule having a CFTR biological characteristic.

The term "plasmid" and "vector" refer to an autonomous self-replicating extrachromosomal circular DNA and includes both the expression and non-expression types. When a recombinant microorganism or cell culture providing expression of a molecule is described as hosting an expression plasmid, the term "expression plasmid" includes both extrachromosomal circular DNA and DNA that has been incorporated into the host chromosome(s).

The term "promoter" is a region of DNA involved in binding RNA polymerase to initiate transcription.

The term "DNA sequence" refers to a single- or double-stranded DNA molecule comprised of nucleotide bases, adenosine (A), thymidine (T), cytosine (C) and guanosine (G) and further includes genomic and complementary DNA (cDNA).

The term "ligate" refers to the joining of DNA fragments via a covalent phosphodiester bond, whose formation is catalyzed for example, by the enzyme T4 DNA ligase.

The term "upstream" identifies sequences proceeding in the opposite direction from expression; for example, the bacterial promoter is upstream from the transcription unit.

The term "restriction endonuclease", alternatively referred to herein as a restriction enzyme, refers to one of a class of enzymes which cleave double-stranded DNA (dsDNA) at locations or sites characteristic to the particular enzyme. For example the restriction endonuclease Eco RI cleaves dsDNA only at locations:

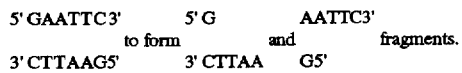

Although many such enzymes are known, the most preferred embodiments of the present invention are primarily concerned with only selected restriction enzymes having specified characteristics.

Within illustrations of plasmid constructions, only restriction endonuclease cleavage sites relevant to the particular construction being depicted are shown. Numbering of nucleotides and amino acids correspond to the published CFTR cDNA sequence of Riordan et al., compiled from partial CFTR cDNA clones.

The term "subject" is intended to include living organisms susceptible to CF, e.g. mammals. Examples of subjects include humans, dogs, cats, horses, cows, goats, rats and mice. The term "subject" further is intended to include transgenic species.

The language "protein enhancing agent" is intended to include agents capable of increasing the intracellular level of at least one cellular protein in a CF-associated cell. The protein enhancing agent can increase the expression of the protein by any mechanism as long as the end result is an increased level of at least one cellular protein. For example, the protein enhancing agent can enhance transcription and/or translation. Examples of protein enhancing agents include carboxylates, carboxylic acids, transcription factors (e.g., AP1, PU. 1) and proto-oncogenes which enhance transcription. An example of a specific protein enhancing agent is butyrate, particularly sodium butyrate.

The preferred protein enhancing agents of the present invention are those having the following formula:

(I)

wherein R has one to five carbon atoms and is a moiety selected from the group consisting of alkyl, alkenyl, and alkynyl; and X is hydrogen or a pharmaceutically acceptable salt.

The alkyl, alkenyl, and alkynyl groups (hereinafter "hydrocarbon groups") can be straight or branched chain moieties. The unsaturated groups can have a single site of unsaturation or a plurality of sites of unsaturation. The hydrocarbon groups can contain up to about five carbon atoms, more preferably up to about four carbon atoms, most preferably up to about three carbon atoms. Examples of hydrocarbon groups which can be used in the present invention include methyl, ethyl, ethenyl, ethynyl, propyl, propenyl, propynyl, butyl, butyenyl, butynyl. Examples of branched chain groups include isobutyl and isopropyl.

The language "differentiating agent" is intended to include an agent capable of inducing the differentiation of a cell. Examples of such agents include retinoic acid, other TPA (phorbol esters), DMSO, DMF, interleukins, and proto-oncogenes capable of inducing differentiation.

The language "carboxy-compound" is intended to include compounds which contain a carboxy group

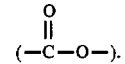

Examples of subgenuses of carboxy-compounds include carboxylic acids and carboxylates. Examples of species of carboxy-compounds include butyric acid and butyrate. The preferred carboxy-compounds are those of formula (I) described above.

The language "pharmaceutically acceptable salt" is art-recognized terminology. Typically these salts are capable of being hydrolyzed or solvated under physiological conditions. Examples of such salts include, sodium, potassium, and hemisulfate. The term further is intended to include lower hydrocarbon groups capable of being hydrolyzed or solvated under physiological conditions, i.e. groups which esterify the carboxyl group, e.g. methyl, ethyl, and propyl.

The protein enhancing agents of the present invention can be purchased or alternatively can by synthesized using conventional techniques. For example, butyrate, particularly sodium butyrate is commercially available.

The language "effective amount" is intended to include that amount sufficient or necessary to significantly reduce or eliminate a subject's symptoms associated with CF. The amount can be determined based on such factors as the type and severity of symptoms being treated, the weight and/or age of the subject, the previous medical history of the subject, and the selected route for administration of the agent. The determination of appropriate "effective amounts" is within the ordinary skill of the art. This definition applies throughout the present application for all agents including protein enhancing agents, differentiating agents and carboxy-compounds. The term "agent" will be used throughout to refer to these substances collectively.

The term "administration" is intended to include routes of administration which allow the agent (e.g., protein enhancing agent) to perform its intended function, e.g., increasing the level of at least one cellular protein. Examples of routes of administration which can be used include injection (subcutaneous, intravenous, parenterally, intraperitoneally, etc.), oral, inhalation, transdermal, and rectal. Depending on the route of administration, the agent can be coated with or in a material to protect it from the natural conditions which may detrimentally effect its ability to perform its intended function. The administration of the agent is done at dosages and for periods of time effective to significantly reduce or eliminate the symptoms associated with CF. Dosage regimes may be adjusted for purposes of improving the therapeutic response of the agent. For example, several divided doses may be administered daily or the dose may be proportionally reduced as indicated by the exigencies of the therapeutic situation.

The language "CF-associated cell" is intended to include a cell associated with CF which contains normal and/or mutant CFTR. Examples of such cells include airway epithelial cells such as nasal and lung epithelia.

The language "increase the intracellular level of a cellular protein" is intended to include an increase of the intracellular-level of cellular protein over that level within the cell prior to treatment with the respective agent. The mode for measuring this increase is not an important aspect of this invention as long as it provides a means for comparing the pre-and post-treatment levels. The cellular protein which is increased can be any protein present within the cell. The cellular protein which is increased preferably is CFTR or mutant CFTR.

The terms "CFTR" and "mutant" "CFTRs" are intended to include normal cystic fibrosis transmembrane regulator and mutant cystic fibrosis transmembrane regulator. The sequence of both the DNA encoding the regulators and the proteins were described previously in the copending applications identified under the Related Applications section. The mutant CFTR proteins include proteins having mutations introduced at residues known to be altered in CF chromosomes (ΔG508, ΔI507, R334W, S5491, G551D) and at residues believed to play an important role in the function of CFTR (e.g., K464N, F508R, N894, 900Q, K1250M).

All cited references are full incorporated herein by reference, subsequent citations of previously cited references shall be by author only. Referenced citations, if not within the body of the text, may be found at the end hereof.

Methods for Treating Cystic Fibrosis

Cystic fibrosis (CF) is a well-known disease state. CF is a disease of infants, children, adolescents, and young adults involving the exocrine glands, especially those secreting mucus. Symptoms associated with CF include pancreatic insufficiency, chronic pulmonary disease, abnormally high sweat electrolyte levels, and, in some cases, cirrhosis of the liver.

The discovery presented herein, that the majority of cases of cystic fibrosis are caused by the absence of mature CFTR and possibly, in the case of pancreatic insufficiency, by the additional deleterious effects of incorrectly located, partially active CFTR, suggests the basis of approaches to CF therapy. One approach is to subject cells containing mutant forms of CFTR which retain at least some functional activity to conditions that alter the subcellular distribution of the mutant proteins.

Wild-type CFTR expressed in 3T3 fibroblasts at 37° C. is present in three forms: band A is unglycosylated protein; band B is core glycosylated protein, which is sensitive to endoglycosidase H, a feature associated with processing in the endoplasmic reticulum; and band C is mature CFTR, which is more extensively glycosylated, a characteristic of processing in the Golgi complex. In contrast, CFTR ΔF508 expressed in cells at 37° C. is present predominantly in bands A and B, suggesting that the protein does not reach the Golgi Complex (Cheng et al. Cell 83:827–834 (1990); Gregory Mol. Cell.Biol. 11:3866–3893 (1991)) Glycosylation per se does not alter the movement or function of CFTR (Gregory Mol. Cell.Biol. 11:3886–3893 (1991)), rather it is a marker of protein processing.

The results of experiments described in detail in the following Examples show that when 3T3 fibroblast cells are grown at lower temperatures for a period of time, a shift in the glycosylation pattern of CFTR ΔF508 towards that of more mature protein (band C) occurs. In contrast, the glycosylation pattern of wild type CFTR does not change. FIG. 14 shows these results graphically. A similar effect of temperature on the glycosylation of CFTR ΔF508 in C127 cells using a different expression system has also been observed. These results indicate that at reduced temperatures, there is an increased flux of the mutant protein through the Golgi complex.

Further, it was observed that as the length of incubation at a reduced temperature is increased (from 6 hrs. to 96 hrs.), the percent of CFTR ΔF508 present in the fully glycosylated form progressively increases. Moreover, the effect is reversible. When the cells were first incubated for two days at 26° C. and then returned to 37° C., the amount of mutant protein present as band C decreased with a half-life of about 7 hrs., a value similar to that observed for wild-type CFTR. Presumably under these conditions, the mature CFTR ΔF508 produced at 26° C. turns over and is not replaced by maturation of new protein.

That processing of the nascent protein is influenced by temperature was further confirmed by pulse-chase experiments which showed that mutant protein synthesized at 37° C. is processed normally during subsequent incubation at 26° C. but not at 37° C.

To confirm that at reduced temperatures CFTR is delivered to the plasma membrane, where it could mediate Cl–transport, a whole-cell patch-clamp technique was used to measure cAMP-activated currents in the plasma membrane of cells expressing CFTRΔF508. (all patch-clamping was at 35° C.).

As reported previously, (Rich, D. P. et al. Nature 347: 355–363 (1990); Anderson, et al., Science 251:679–682 (1991)), cAMP agonists failed to stimulate Cl– currents in cells cultured at 37° C. But after incubation at 30° C. for 2 days, cAMP agonists stimulated large chloride-selective currents. The same results were obtained in C127 cells expressing CFTR ΔF508. Just as with the production of band C, when the temperature was returned to 37° C. for 24 hours, the size of the cAMP-stimulated current decreased. The cAMP-stimulated Cl– current was found to have a linear current—voltage relationship, to be selective for Cl–over Na+ and to show little time-dependent voltage effects. These properties are similar to those found with wild-type channels. (Anderson, et al. Science 251:679–682 (1991)).

To confirm that the current results from expression of CFTR ΔF508 and to determine whether the ΔF508 mutation alters the properties of CFTR, single-channel currents were measured using excised, inside-out patches of membrane. As with wild-type CFTR, there was found to be little basal channel activity in excised patches. Addition of ATP to the cytosolic surface caused no activation, but a combination of ATP plus the catalytic subunit of cAMP-dependent protein kinase (protein kinase A; PKA) activated multiple channels.

The current-voltage relationship was linear and the single-channel current at −100 mV was −1.1 ±0.0 pA(n=6), compared to −1.1±0.0 pA(n=7), for wild-type channels under similar conditions. When ATP and PKA were removed, activity returned to basal values. Despite these apparently normal biophysical properties and the normal regulation by cAMP (in the whole cell) and PKA (in excised patches), the channels had a reduced probability of being in the open state $(P_o)$ at 1 mM ATP; $P_o$ was 0.34±0.02 (n=14) for wild-type CFTR and 0.13±0.01 (n=4) for CFTR ΔF508. The reduced $P_o$ of CFTR ΔF508 is similar to the value previously reported.

The above results indicate that the processing of CFTR mutant such as CFTR ΔF508 reverts towards that of wild-type as the temperature is reduced. When the processing defect is so corrected, cAMP-regulated Cl– channels appear in the cell's plasma membrane. The major cause of morbidity and mortality in cystic fibrosis is lung disease. The findings disclosed herein suggest that the adverse effects of mutant CFTR in the lung can be prevented or treated by exposing the patient's lung epithelia to a temperature below normal body temperature (37° C.) for a period of time sufficient to mobilize the mutant CFTR to the plasma membrane of the lung epithelia, where it can mediate chloride ion transport. Inhalation of cold air during hyperventilation has been shown to reduce airway temperature to values approaching 30° C. (Gilbert, et al., J. Appl. Physiol.

63:1681–1691 (1987)). Therefore, having a patient inhale air of a temperature lower than 37° C. and preferably in the range of 20°–30° C. for an appropriate period of time may be useful for mobilizing mutant CFTR to the plasma membrane where they can function in the ion transport. Alternatively, a nontoxic agent capable of lowering the temperature in the vicinity of the lung to a temperature below 37° C. can be implanted in the patient's lung.

The present invention pertains to a method for treating a subject having cystic fibrosis (CF). The method involves the administration of a protein enhancing agent to a subject having CF. The protein enhancing agent increases the intracellular level of at least one cellular protein in a CF-associated cell such that a mutant cystic fibrosis transmembrane regulator (CFTR) protein generates functional chloride channels in the CF-associated cell of the subject.

The present invention further provides the discovery that the treatment of cystic fibrosis-associated (CF-associated) cells with butyrate results in functional mutant cystic fibrosis transmembrane regulator (CFTR) protein within the CF-associated cells. The butyrate facilitates the delivery of the mutant CFTR to the appropriate location within the CF-associated cell (the plasma membrane) and the mutant CFTR of butyrate-treated cells are capable of generating chloride channels.

Butyrate is a well known differentiating agent. Butyrate also is a protein enhancing agent in that the addition of butyrate to the CF-associated cell, e.g. an increased level of mutant CFTR. The increased level of intracellular protein can lead to the passage of the mutant CFTR by the surveillance of the quality control mechanism present in the endoplasmic reticulum of the CF-associated cell allowing the delivery of the mutant CFTR to the plasma membrane.

The present invention even further pertains to a method for treating a subject's lung epithelia containing a mutant CFTR protein. The method involves contacting a subject's lung epithelia with the protein enhancing agent which increases the level of at least one cellular protein such that a mutant CFTR protein present in the lung epithelia mediates chloride ion transport across the cell membrane. The subject's lung epithelia can be contacted by administrating the protein enhancing agent to the subject.

The present invention further pertains to a method for treating a subject having CF by administering an effective amount of a differentiating agent to the subject. The differentiating agent is administered such that a mutant CFTR present in the CF-associated cells of the subject generates functional chloride channels or mediates chloride ion transport.

The present invention further pertains to a method for treating a subject having CF by administering an effective amount of a carboxy-compound to the subject. The carboxy-compound is administered such that a mutant CFTR present in CF-associated cells of the subject generates functional chloride channels or mediates chloride ion transport.

The present invention further pertains to therapeutic compositions for treating a subject having CF. The composition contains a therapeutically affective amount of a forementioned agent (protein enhancing agent, differentiating agent, and/or carboxy-compound) and a pharmaceutically acceptable carrier.

The language "therapeutically effective amount" is that amount sufficient or necessary to significantly reduce or eliminate a subject's symptoms associated with CF. The amount can vary depending on such factors as the severity of the symptoms being treated, the size of the subject, or the selected route for administration of the agent.

The language "pharmaceutically acceptable carrier" is intended to include substances capable of being co-administered with the agent and which allow the agent to perform its intended function, e.g. increasing the intracellular level of at least once cellular protein or inducing differentiation. Examples of such carriers include solvents, dispersion media, delay agents and the like. The use of such media and agents for pharmaceutically active substances is well known in the art. Any conventional media and agent compatible with the agent can be used with this invention. The agent of this invention can be administered alone or in a pharmaceutically accepted carrier. The agents further can be administrated as a mixture of agents which also can be in a pharmaceutically acceptable carrier. The agent further can be co-administered with other different art-recognized protein enhancing agents, differentiating agents, and/or adjuvants.

The present invention further pertains to a packaged drug for treating a subject having CF. The packaged drug includes a container holding an agent described above and instructions for administering the agent for treating a subject having CF. Examples of containers include vials, syringes, etc. The instructions would contain dosage information for administering the agent as described above.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLE 1

Generation of Full length CFTR cDNAs

Nearly all of the commonly used DNA cloning vectors are based on plasmids containing modified pMB1 replication origins and are present at up to 500 to 700 copies per cell (Sambrook et al.). The partial CFTR cDNA clones isolated by Riordan et al. were maintained in such a plasmid. We postulated that an alternative theory to intrinsic clone instability to explain the apparent inability to recover clones encoding full length CFTR protein using high copy number plasmids, was that it was not possible to clone large segments of the CFTR cDNA at high gene dosage in E. coli. Expression of the CFTR or portions of the CFTR from regulatory sequences capable of directing transcription and/ or translation in the bacterial host cell might result in inviability of the host cell due to toxicity of the transcript or of the full length CFTR protein or fragments thereof. This inadvertent gene expression could occur from either plasmid regulatory sequences or cryptic regulatory sequences within the recombinant CFTR plasmid which are capable of functioning in E. coli. Toxic expression of the CFTR coding sequences would be greatly compounded if a large number of copies of the CFTR cDNA were present in cells because a high copy number plasmid were used. If the product was indeed toxic as postulated, the growth of cells containing full length and correct sequence would be actively disfavored. Based upon this novel hypothesis, the following procedures were undertaken.

Figure 2:
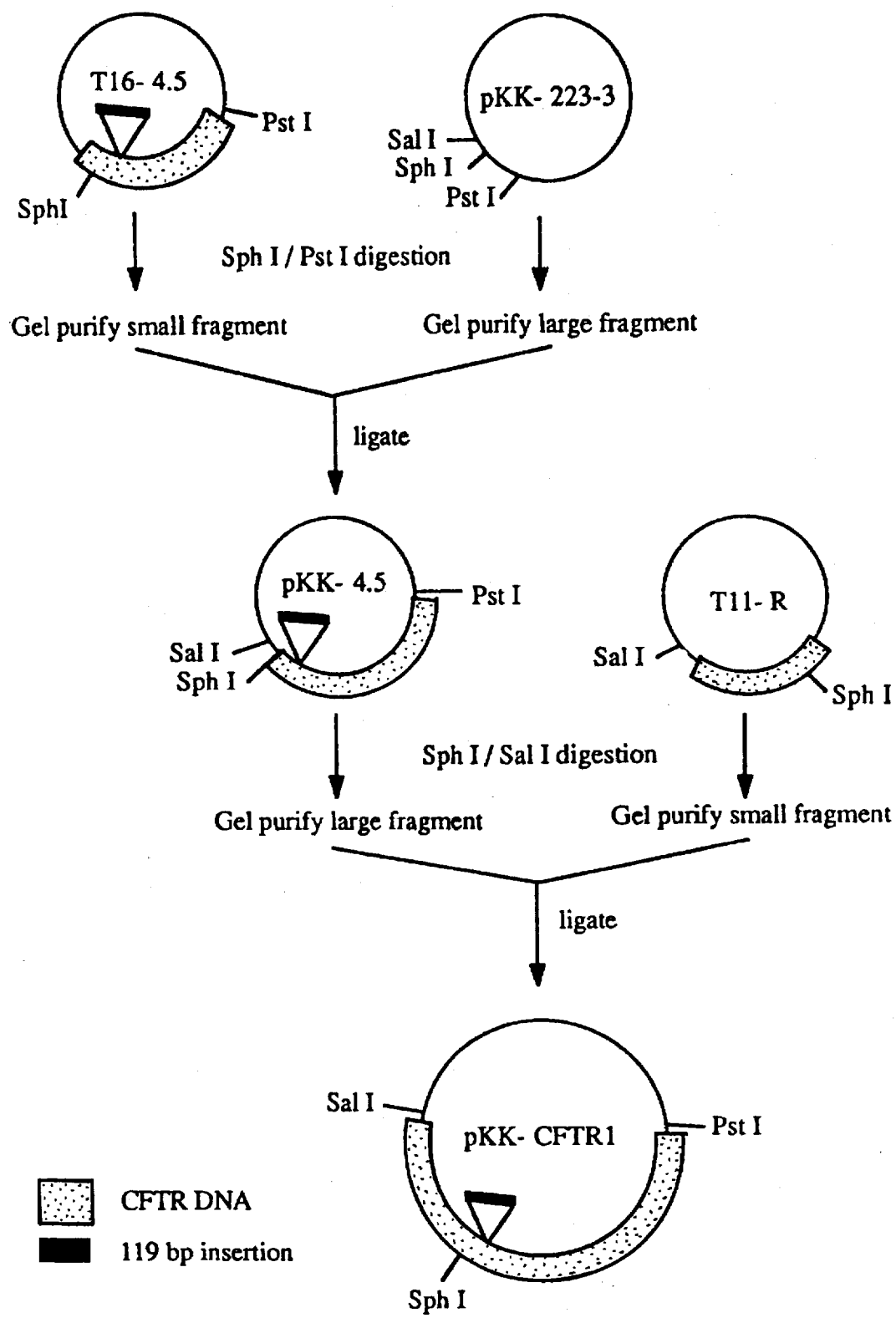
FIG. 2 depicts plasmid construction of the CFTR cDNA clone pKK-CFTR1.

With reference to FIG. 2, partial CFTR clone T16–4.5 was cleaved with restriction enzymes Sph I and Pst I and the resulting 3.9 kb restriction fragment containing exons 11 through most of exon 24 (including an uncharacterized 119 bp insertion reported by Riordan et al. between nucleotides 1716 and 1717), was isolated by agarose gel purification and ligated between the Sph I and Pst I sites of the pMB1 based vector pKK223-3 (Brosius and Holy, *Proc. Natl. Acad. Sci.* 81, 6929 (1984)). It was hoped that the pMB1 origin contained within this plasmid would allow it and plasmids constructed from it to replicate at 15–20 copies per host *E. coli* cell (Sambrook et al.). The resultant plasmid clone was called pKK-4.5.

Partial CFTR clone T11 was cleaved with Eco RI and Hinc II and the 1.9 kb band encoding the first 1786 nucleotides of the CFTR cDNA plus an additional 100 bp of DNA at the 5' end was isolated by agarose gel purification. This restriction fragment was inserted between the Eco RI site and Sma I restriction site of the plasmid pBluescript Sk– (Stratagene, catalogue number 212206), such that the CFTR sequences were now flanked on the upstream (5') side by a Sal I site from the cloning vector. This clone, designated T11-R, was cleaved with Sal I and Sph I and the resultant 1.8 kb band isolated by agarose gel purification. Plasmid pKK-4.5 was cleaved with Sal I and Sph I and the large fragment was isolated by agarose gel purification. The purified CFTR 1 contains exons 1 through 24 of the CFTR cDNA. It was discovered that this plasmid is stably maintained in *E. coli* cells and confers no measurably disadvantageous growth characteristics upon host cells.

pKK-CFTR1 contains, between nucleotides 1716 and 1717, the 119 bp insert DNA derived from partial cDNA clone T16–4.5 described above. In addition, subsequent sequence analysis of pKK-CFTR1 revealed unreported differences in the coding sequence between that portion of CFTR1 derived from partial cDNA clone T11 and the published CFTR cDNA sequence. These undesired differences included a 1 base-pair deletion at position 995 and a C to a T transition at position 1507.

Figure 3:
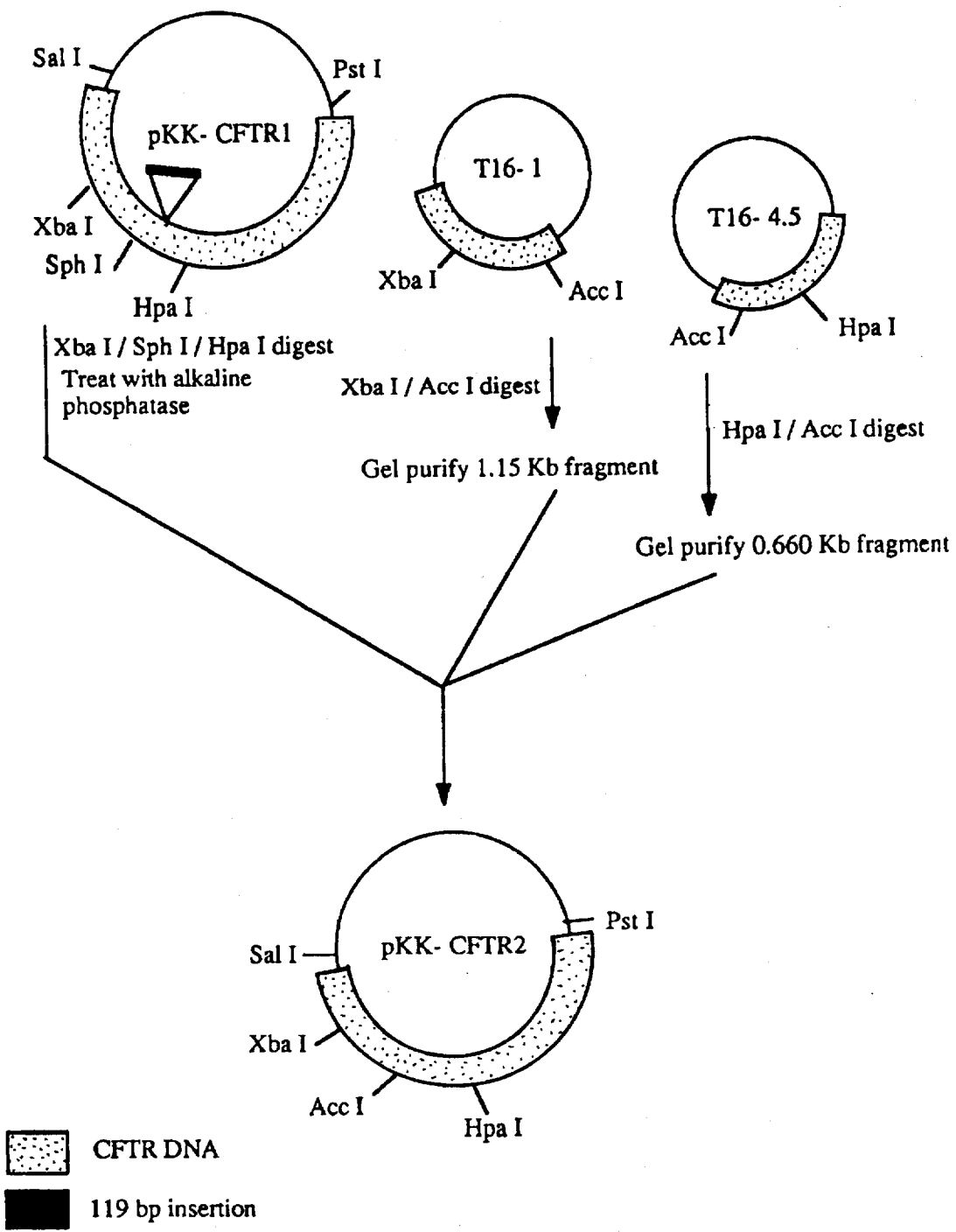
FIG. 3 depicts plasmid construction of the CFTR cDNA clone pKK-CFTR2.

To complete construction of an intact correct CFTR coding sequence without mutations or insertions and with reference to the construction scheme shown in FIG. 3, pKK-CFTR1 was cleaved with Xba I and Hpa I, and dephosphorylated with calf intestinal alkaline phosphatase. In addition, to reduce the likelihood of recovering the original clone, the small unwanted Xba I/Hpa I, restriction fragment from pKK-CFTR1 was digested with Sph I. T16–1 was cleaved with Xba I and Acc I and the 1.15 kb fragment isolated by agarose gel purification. T16–4.5 was cleaved with Acc I and Hpa I and the 0.65 kb band was also isolated by agarose gel purification. The two agarose gel purified restriction fragments and the dephosphorylated pKK-CFTR1 were ligated to produce pKK-CFTR2. Alternatively, pKK-CFTR2 could have been constructed using corresponding restriction fragments from the partial CFTR cDNA clone C1–1/5. pKK-CFTR2 contains the uninterrupted CFTR protein coding sequence and conferred slow growth upon *E. coli* host cells in which it was inserted, whereas pKK-CFTR1 did not. The origin of replication of pKK-CFTR2 is delivered from pMB1 and confers a plasmid copy number of 15–20 copies per host cell.

EXAMPLE 2

Improving Host Cell Viability

An additional enhancement of host cell viability was accomplished by a further reduction in the copy number of CFTR cDNA per host cell. This was achieved by transferring the CFTR cDNA into the plasmid vector, pSC-3Z. pSC-3Z was constructed using the pSC101 replication origin of the low copy number plasmid pLG338 (Stoker et al., *Gene* 18, 335 (1982)) and the ampicillin resistance gene and polylinker of pGEM-3Z (available from Promega). pLG338 was cleaved with Sph I and PvU II and the 2.8 kb fragment containing the replication origin isolated by agarose gel purification. pGEM-3Z was cleaved with Alw NI, the resultant restriction fragment ends treated with T4 DNA polymerase and deoxynucleotide triphosphates, cleaved with Sph I and the 1.9 kb band containing the ampicillin resistance gene and the polylinker was isolated by agarose gel purification. The pLG338 and pGEM-3Z fragments were ligated together to produce the low copy number cloning vector pSC-3Z. pSC-3Z and the other plasmids containing pSC101 origins of replication are maintained at approximately five copies per cell (Sambrook et al.).

Figure 4:
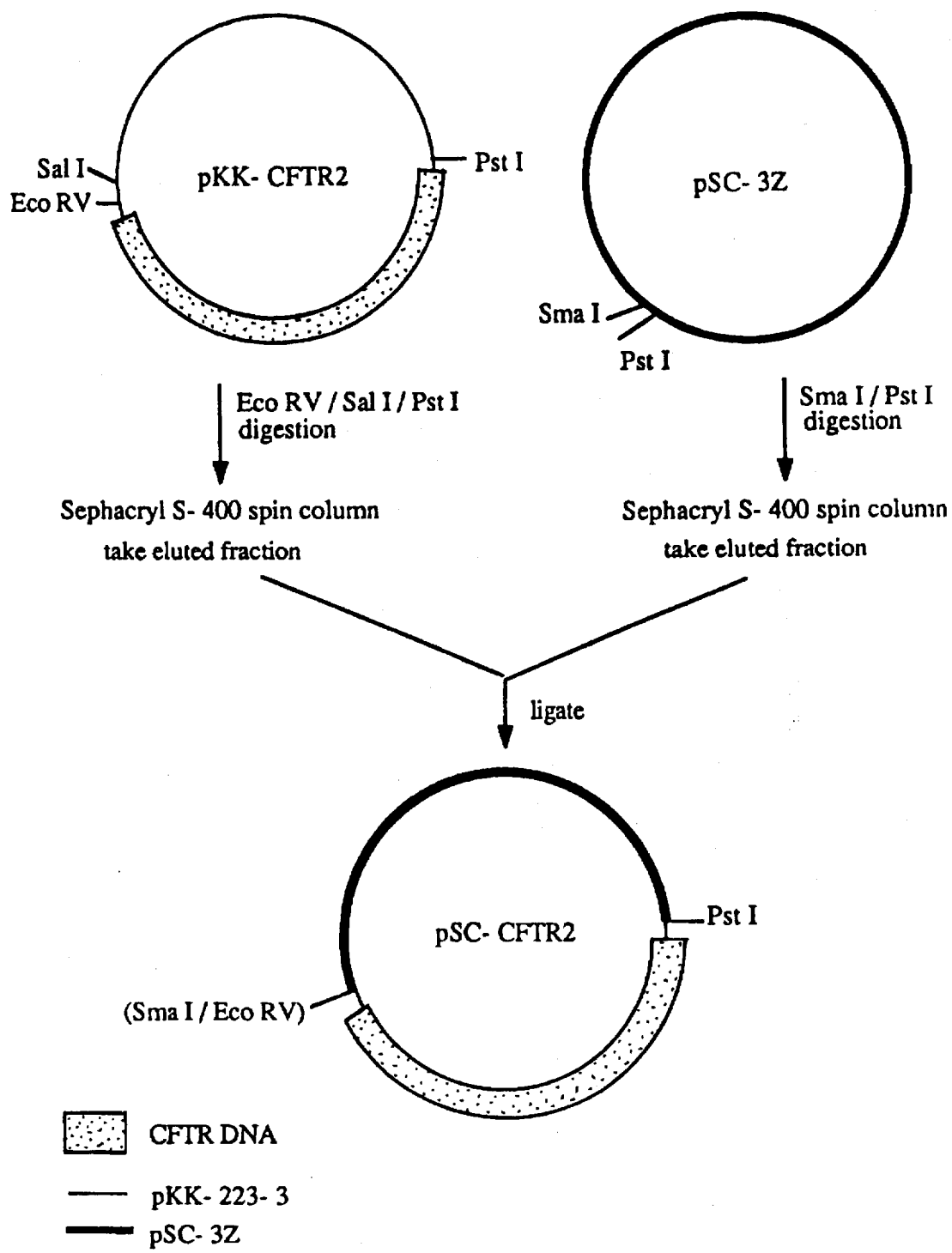
FIG. 4 depicts plasmid construction of the CFTR cDNA clone pSC-CFTR2.
Figure 5:
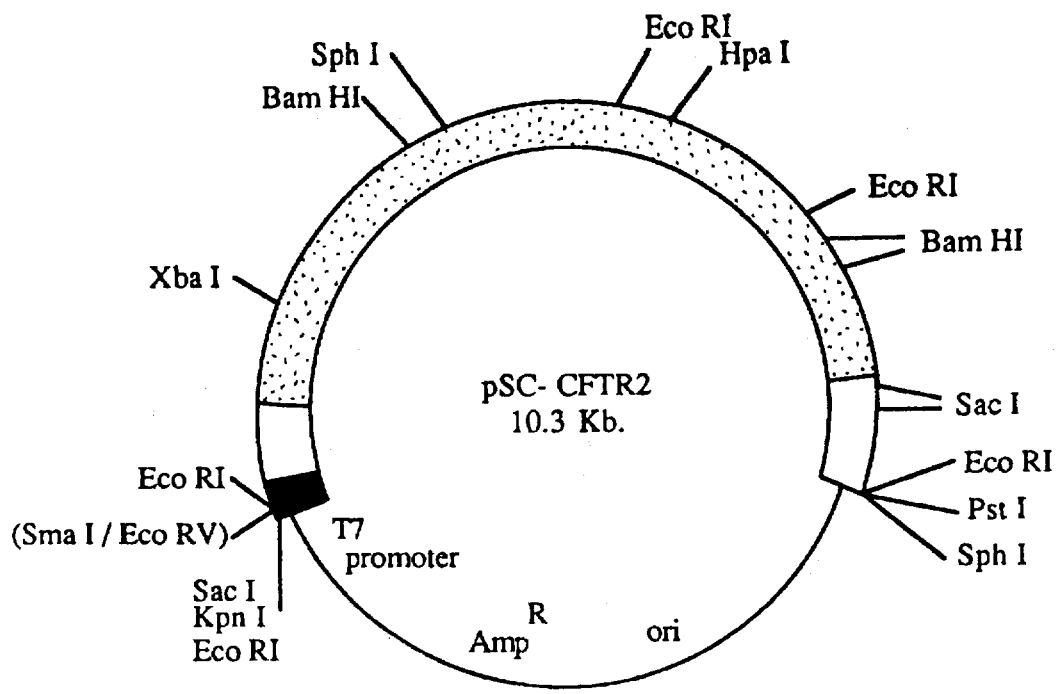
FIG. 5 shows a plasmid map of the CFTR cDNA clone pSC-CFTR2.

With additional reference to FIG. 4, pKK-CFTR2 was cleaved with Eco RV, Pst I and Sal I and then passed over Sephacryl S400 spun column (available from Pharmacia) according to the manufacturer's procedure in order to remove the Sal I to Eco RV restriction fragment which was retained within the column. pSc-3Z was digested with Sma I and Pst I and also passed over a Sephacryl S400 spun column to remove the small Sma I/Pst I restriction fragment which was retained within the column. The column eluted fractions from pKK-CFTR2 digest and the pSC-CFTR2 digest and the pSC-3Z digest were mixed and ligated to produce pSC-CFTR2. A map of this plasmid is presented in FIG. 5. Host cells containing CFTR cDNAs at this and similar gene dosages grow well and have stably maintained the recombinant plasmid with the full length CFTR coding sequence. In addition, this plasmid contains a bacteriophage T7 RNA polymerase promoter adjacent to the CFTR coding sequence and is therefore convenient for in vitro transcription/translation of the CFTR protein. The nucleotide sequence of CFTR coding region from pSC-CFTR2 plasmid is presented in Table 1. Significantly, this sequence differs from the previously published (Riordan et al.) CFTR sequence at position 1991, where there is C in place of the reported A. *E. coli* host cells containing pSC-CFTR2, internally identified with the number pSC-CFTR2/AG1, have been deposited at the American Type Culture Collection and given the accession number: ATCC 68244.

EXAMPLE 3

Alternate Method for Improving Host Cell Viability

Figure 7A:
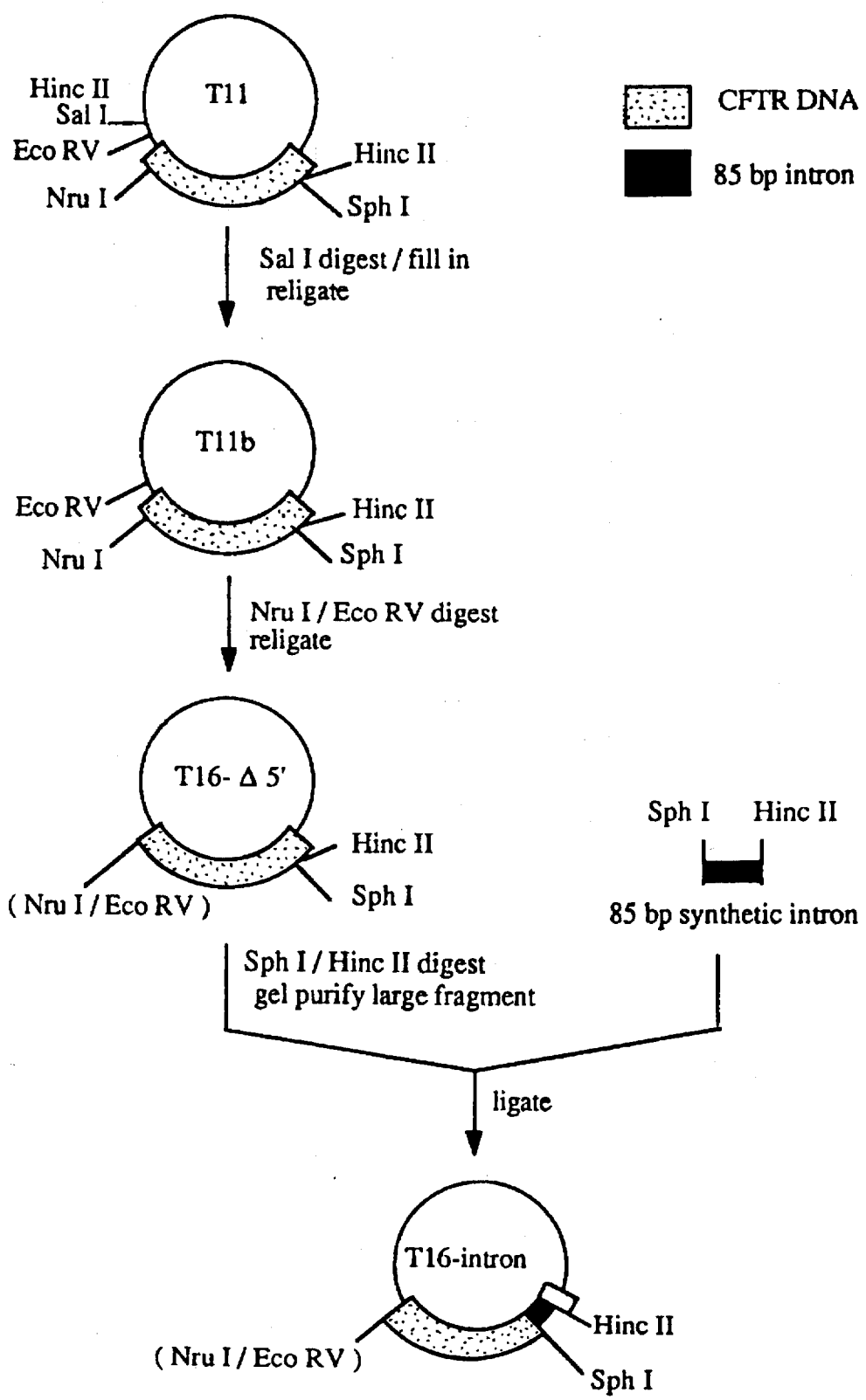
FIGS. 7A and 7B depict plasmid construction of the CFTR cDNA clone pKK-CFTR3.
Figure 7B:
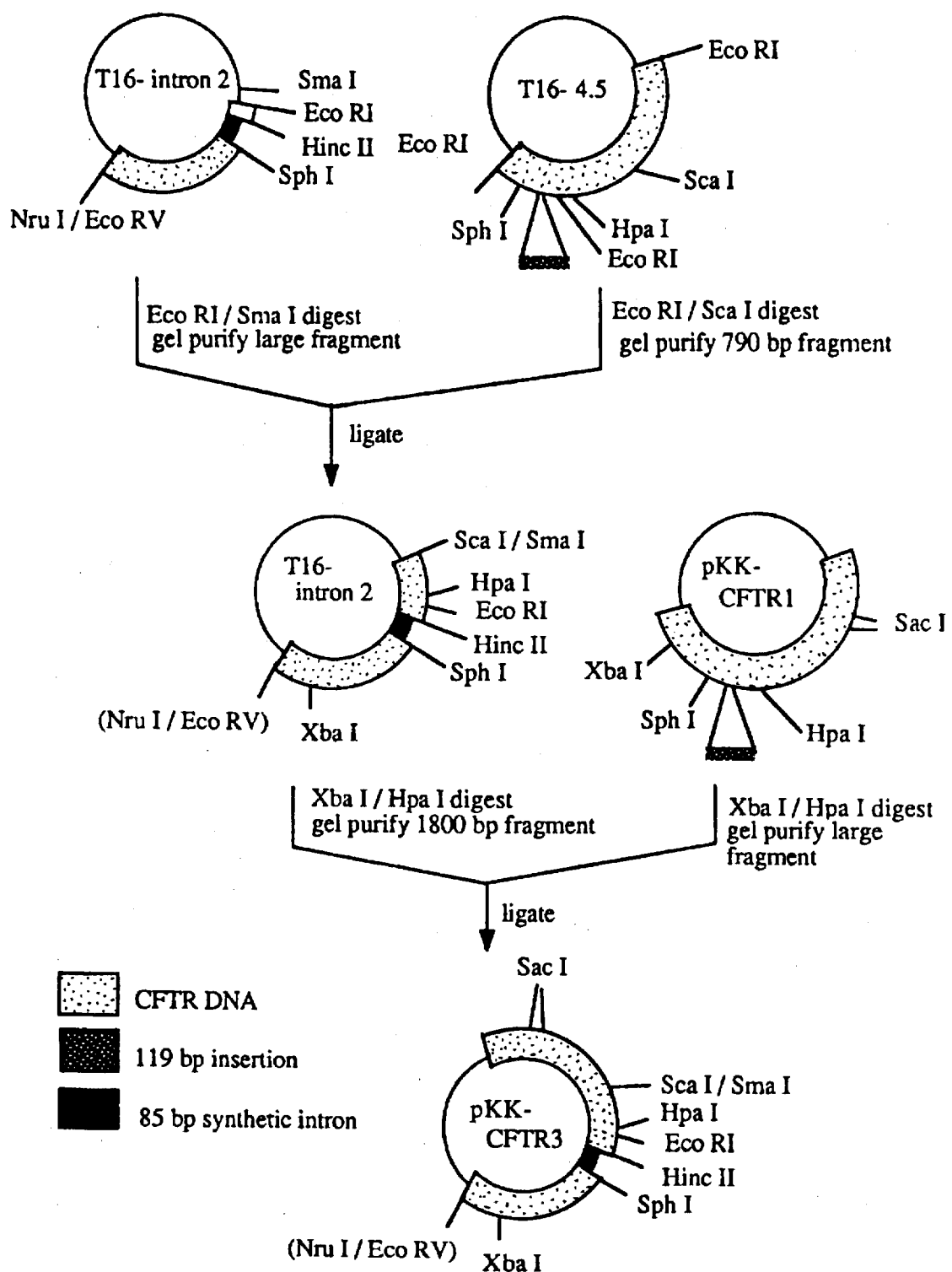

A second method for enhancing cell viability comprises disruption of the CFTR protein coding sequence. For this purpose, a synthetic intron was designed for insertion between nucleotides 1716 and 1717 of the CFTR cDNA. This intron is especially advantageous because of its easily manageable size. Furthermore, it is designed to be efficiently spliced from CFTR primary RNA transcripts when expressed in eukaryotic cells. Four synthetic oligonucleotides were synthesized (1195RG, 1196RG, 1197RG and 1198RG) collectively extending from the Sph I cleavage site at position 1700 to the Hinc II cleavage site at position 1785 and including the additional 83 nucleotides between 1716 and 1717 (see FIG. 6). These oligonucleotides were phosphorylated with T4 polynucleotide kinase as described by Sambrook et al., mixed together, heated to 95° C. for 5 minutes in the same buffer used during phosphorylation, and allowed to cool to room temperature over several hours to allow annealing of the single stranded oligonucleotides. To insert the synthetic intron into the CFTR coding sequence and with reference to FIGS. 7A and 7B, a subclone of plasmid T11 was made by cleaving the Sal I site in the polylinker, repairing the recessed ends of the cleaved DNA with deoxynucleotide triphosphates and the large fragment of DNA Polymerase I and religating the DNA. This plasmid was then digested with Eco RV and Nru I and religated. The resulting plasmid T16-Δ5' extended from the Nru I site at position 490 of the CFTR cDNA to the 3' end of clone T16 and contained single sites for Sph I and Hinc II at positions corresponding to nucleotides 1700 and 1785 of the CFTR cDNA. T16-Δ5' plasmid was cleaved with Sph I and Hinc II and the large fragment was isolated by agarose gel purification. The annealed synthetic oligonucleotides were ligated into this vector fragment to generate T16-intron.

T16-intron was then digested with Eco RI and Sma I and the large fragment was isolated by agarose gel purification. T16–4.5 was digested with Eco RI and Sca I and the 790 bp fragment was also isolated by agarose gel purification. The purified T16-intron and T16–4.5 fragments were ligated to produce T16-intron-2. T16-intron-2 contains CFTR cDNA sequences extending from the Nru I site at position 490 to the Sca I site at position 2818, and includes the unique Hpa I site at position 2463 which is not present in T16–1 or T16-intron-1.

Figure 8:
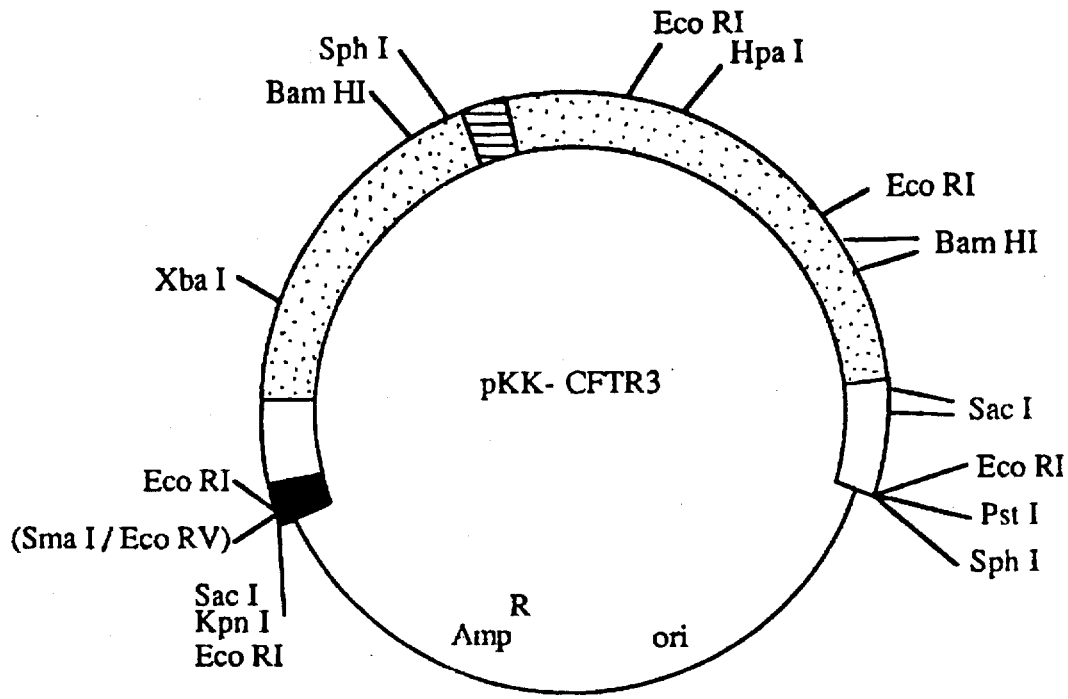
FIG. 8 shows a plasmid map of the CFTR cDNA pKK-CFTR3 containing an intron between nucleotides 1716 and 1717.

T16-intron-2 was then cleaved with Xba I and Hpa I and the 1800 bp fragment was isolated by agarose gel purification. pKK-CFTR 1 was digested with Xba I and Hpa I and the large fragment was also isolated by agarose gel purification and ligated with the fragment derived from T16-intron-2 to yield pKK-CFTR3, shown in FIG. 8. The CFTR cDNA within pKK-CFTR3 is identical to that within pSC-CFTR2 and pKK-CFTR2 except for the insertion of the 83 bp intron between nucleotides 1716 and 1717. The insertion of this intron resulted in improved growth characteristic for cells harboring pKK-CFTR3 relative to cells containing the unmodified CFTR cDNA in pKK-CFTR2.

EXAMPLE 4

In vitro Transcription/Translation

In addition to sequence analysis, the integrity of the CFTR cDNA open reading frame was verified by in vitro transcription/translation. This method also provided the initial CFTR protein for identification purposes. 5 µg of pSC-CFTR2 plasmid DNA were linearized with Sal I and used to direct the synthesis of CFTR RNA transcripts with T7 RNA polymerase as described by the supplier (Stratagene). This transcript was extracted with phenol and chloroform and precipitated with ethanol. The transcript was resuspended in 25 µl of water and varying amounts were added to a reticulocyte lysate in vitro translation system (from Promega). The reactions were performed as described by the supplier in the presence of canine pancreatic microsomal membranes (from Promega), using $^{35}$S-methionine to label newly synthesized proteins. In vitro translation products were analyzed by discontinuous polyacrylamide gel electrophoresis in the presence of 0.1% SDS with 8% separating gels (Laemmli, 1970). Before electrophoresis, the in vitro translation reactions were denatured with 3% SDS, 8M urea and 5% β-mercaptoethanol in 0.65M Tris-HCl, pH 6.8. Following electrophoresis, the gels were fixed in methanol:acetic acid:water (30:10:60), rinsed with water and impregnated with 1M sodium salicylate. $^{35}$S labeled proteins were detected by fluorograph. A band of approximately 180 Kd was detected, consistent with translation of the full length CFTR insert.

EXAMPLE 5

Elimination of Cryptic Regulatory Signals

Analysis of the DNA sequence of the CFTR has revealed the presence of a potential *E. coli* RNA polymerase promoter between nucleotides 748 and 778 which conforms well to the derived consensus sequence for *E. Coli* promoters (Reznikoff and McClure, *Maximizing Gene Expression*, 1, Butterworh Publishers, Stoneham, Mass.). If this sequence functions as a promoter functions in *E. coli*, it could direct synthesis of potentially toxic partial CFTR polypeptides. Thus, an additional advantageous procedure for maintaining plasmids containing CFTR cDNAs in *E. coli* would be to alter the sequence of this potential promoter such that it will not function in *E. coli*. This may be accomplished without altering the amino acid sequence encoded by the CFTR cDNA. Specifically, plasmids containing complete or partial CFTR cDNAs would be altered by site-directed mutagenesis using synthetic oligonucleotides (Zoeller and Smith, *Methods Enzymol.* 100 468, 1983). More, specifically, altering the nucleotide sequence at position 908 from a T to a C and at position 774 from an A to a G effectively eliminates the activity of this promoter sequence without altering the amino acid coding potential of the CFTR open reading frame. Other potential regulatory signals within the CFTR cDNA for transcription and translation could also be advantageously altered and/or deleted by the same method.

EXAMPLE 6

Cloning of CFTR in alternate host systems

Although the CFTR cDNA displays apparent toxicity in *E-coli* cells, other types of host cells may not be affected in this way. Alternative host systems in which the entire CFTR cDNA protein encoding region may by maintained and/or expressed include other bacterial species and yeast. It is not possible a priori to predict which cells might be resistant and which might not. Screening a number of different host/vector combinations is necessary to find a suitable host tolerate of expression of the full length protein or potentially toxic fragments thereof.

EXAMPLE 7

Productions of CFTR mutants and relevant plasmids constructions

Mutations were introduced into CFTR residues known to be altered in CF chromosomes (ΔF508, ΔI507, R334W, S5491, G551D) and in residues believed to play an important role in the function of CFTR (K464M, F508R N894, 900Q, K1250M). CFTR encoded by these mutants was examined in COS-7 cells transfected with cDNA plasmids having the aforementioned alterations. Remarkably, it was surprisingly discovered that mature, fully glycosylated CFTR was absent from cells containing ΔF508, ΔI507, K464M, F508R and S5491 cDNA plasmids. Instead, an unstable, incompletely glycosylated version of the protein was detected with an apparent molecular weight of 135 kd. Surprisingly, the immature, mutant versions of CFTR appear to be recognized as abnormal by a component of the post-translational intracellular transport machinery, and remain incompletely processed in the endoplasmic reticulum where they are subsequently degraded. Since mutations with this phenotype represent at least 70% of known CF chromosomes, we have discovered that the primary cause of cystic fibrosis is the absence of mature CFTR at the correct cellular location, see also FIGS. 10 and 12. As a result of this surprising result, this invention provides new approaches to the diagnosis and treatment of CF.

Recombinant DNA manipulations were performed according to standard methods (Sambrook et al., 1989). Oligonucleotide-directed mutagenesis of the CFTR cDNA was performed as described by Kunkel (1985). A plasmid vector for CFTR expression in mammalian cells was constructed by placing CFTR cDNA sequences from the Ava I site at position 122 in the cDNA sequence to the Sac I site at position 4620 into the unique Bgl II site of the expression vector pSC-CEV1 using synthetic adapter sequences. The resulting plasmid was called pMT-CFTR. In pMT-CFTR, expression of CFTR is controlled by the flanking mouse metallothionein-1promoter and SV40 early polyadenylation signal. The vector also contains an origin of replication from pSC 101 (Cohen, 1973) for replication in *E. coli* the β-lactamase gene and an SV40 origin of replication. For convenient site-directed mutagenesis of CFTR, the cryptic bacterial promoter within the CFTR cDNA of plasmid pMT-CFTR-3 (Gregory et al., 1990) was first inactivated by changing the T residue at nucleotide 936 to a C such that plasmids containing CFTR sequences could be maintained at a high copy number without corresponding changes in amino acid sequence. The CFTR cDNA was then inserted between the Apa I and Sac I sites of the high copy number vector pMT1 (available from T. Mizukami, O. Elroy-Stein and B. Moss, National Institutes of Health) using a 5' flanking Apa I site common to pMT-CFTR-3 and pMT1, and the Sac I site at position 4620 in the CFTR cDNA. This plasmid, pMT-CFTR-4, was used for all subsequent mutagenesis of the CFTR sequence. For expression in COS-7 cells, CFTR cDNA mutants constructed in pMT-CFTR-4 were digested with Xba I and Bst XI and the 3.5 kb CFTR cDNA fragment was purified and placed between the unique Xba I and Bst XI within the CFTR cDNA portion of pMT-CFTR. Transient expression of CFTR in COS-7 cells was performed essentially as described by Sambrook at al., (1989).

EXAMPLE 8

Production of CFTR and Protein Therapy

Protein therapy may be accomplished by using CFTR protein produced by host cells transformed or transfected with the CFTR cDNA of the present invention to correct the CF defect directly by introducing the protein into the membrane of cells lacking functional CFTR protein. This therapeutic approach augments the defective protein by addition of the wild-type molecule. The full length cDNA disclosed here can readily be used via conventional techniques to produce vectors for expression of the CFTR protein in a variety of well known host systems. Protein or membrane fragments purified or derived from these cells can be formulated for treatment of cystic fibrosis.

Recombinant CFTR can be made using techniques such as those reported by Numa (*Harvey Lectures* 83, 121 (1989) and references cited therein) for the synthesis of other membrane proteins under the direction of transfected cDNAs. It will be important to realize that toxicity can result in mammalian cells from over expression of membrane proteins (Belsham et al., *Eur. J. Biochem.* 156 413 (1986)). Fortunately, to circumvent the potential toxicity of the protein product, vectors with inducible promoters (Klessig et al., *Mol. Cell. Biol.* 4, 1354 (1984)) can be advantageously used.

For example, for constitutive expression in mammalian cells, the full length CFTR cDNA clone is constructed so that it contains Xho I sites immediately 5' to the initiator methionine ATG and 3' to the terminator TAG. These sites are unique since there are no Xho I sites in the CFTR cDNA sequence. This facilitates incorporation of the DNA sequence encoding CFTR into expression vectors of the types described below.

Those skilled in the art will recognize that many possible cell/vector systems have been used successfully for the high level expression of recombinant proteins. Several suitable systems are described below. Bovine Papilloma Virus (BPV) based vectors (Hamer and Walling, *J. Mol. Appl. Gen.* 1 273 (1982)) can be used to transform mouse C127 cells. C127 comprise an adenocarcinoma cell line isolated from a mammary tumor of an R111 mouse (ATCC: CRL 1616). Following the procedures of Hsiung et al (*J. Mol. Appl. Gen.* 2, 497 (1984)) and Reddy et al., (DNA 6, 461 (1987)), the BPV vector can be constructed in such a way to express recombinant CFTR protein under control of the mouse metallothionein promoter and polyadenylation sequences. Once a construct containing the CFTR cDNA is made, it is then advantageously transfected into the C127 cells using standard calcium phosphate precipitation methods (Graham and Van der Eb, *Virology* 52, 456 (1973)). The transformed cells can then be selected by foci formation. A similar vector, in which the gene for neomycin resistance (Southern and Berg, *J. Mol, Appl. Gen* 1, 327 (1982)) has been inserted into the same unique Sal I site, may advantageously also be supertransfected into the same cells and cells incorporating such vectors suitably selected with the antibiotic G418. This method conveniently decreases the time necessary to select for desired cell lines expressing the transfected gene product.

Another expression systems employs vectors in which the cDNA is under control of the metallothionein gene promoter and the SV40 early polyadenylation signal. In addition, the mouse dihydrofolate reductase (DHFR) cDNA (Nunberg et al., Cell 19, 355 (1980)) is under control of the SV40 early promoter and polyadenylation signal. This vector is then ideally transfected into Chinese Hamster Ovary (CHO) cells (ATCC: CCL 61) that are deficient in DHFR (Urlaub and Chasin, Proc. Natl. Acad. Sci. 77, 4216 (1980)). Transformed cells can be selected and the CFTR containing vector sequences amplified by culturing the cells in media containing the drug methotrexate.

Yet another example of an inducible expression system involves the use of vectors based upon the commercially available plasmid, pMAMneo (Clontech). pMAMneo contains a mouse mammary tumor virus promoter for expression of cloned genes. This promoter can be induced by treating transfected cells with glucocorticoids, such as dexamethasone, resulting in elevated expression of the cloned gene. The $NA^+/H^+$ antiporter is a membrane protein that is structurally very similar to the CFTR and has been successfully expressed with the pMAMneo vector (Sardet et al., *Cell* 56, 271 (1989)). Vectors based on pMAMneo, but containing low copy number *E. coli* origins of replication, could be used for inducible expression of CFTR in either C127 cells, CHO or other mammalian cells as described above.

Similarly, many suitable expression vector/host system have been describe for the expression of mammalian proteins in bacteria, fungi, insect and plant cells and in the milk of transgenic animals. One skilled in the art can modify these expression systems for the production of CFTR. For example, low copy number CFTR vectors, based upon the invention described herein, could be used to direct synthesis of CFTR protein in *E. coli*. To avoid toxicity due to expression of CFTR RNA or protein, the CFTR cDNA must be under the transcriptional control of a regulatable promoter. As an example of one such inducible expression system, the T7 RNA polymerase promoter within pSC-CFTR2 could be used to induce transcription of CFTR sequences in *E. coli* as described by Studier and Moffet *J. Mol Biol.* 189, 113 (1986). In order to maximize levels of CFTR protein expression after transcriptional induction, it would be necessary to introduce an *E. coli* ribosome binding site (Shine and Dalgarno, *Nature* 254, 43 (1975)) upstream of the CFTR initiator methionine. Prokaryotic organisms other than *E. coli* could also be used for expression of CFTR protein. For example, a membrane-bound phosphotriesterase has been successfully produced in *Streptomyces lividans* by Steiert et al. (*Biotechnology* 7, 65 (1989)).

Owing to the nature of CFTR glycosylation, the most preferred expression systems will utilize mammalian cells. Transient expression of CFTR can be accomplished using COS-7 cells as previously described in Example 7 and in subsequent examples.

Foreign proteins have be expressed using a variety of vectors in many different fungi. For example, van den Berg et al. (*Biotechnology* 8, 135 (1990)) have produced prochymosin in *Kluyveromyces lactis*, Loison et al. (*Biotechnology*, 72 (1988)) produced hirudin in *Saccharomyces cerevisiae*, and Cregg et al. (*Biotechnology* 5, 479 (1987)) have produced hepatitis B surface antigen in *Pichia pastoris*.

For insect cells the β-adrenergic receptor, a membrane protein, has been expressed using a baculovirus expression vector (George et al., *Biochem. Biophys. Res. Comm.* 163 1265 (1989)). CFTR could be produced in insect cells by obvious modification of this system.

CFTR could be expressed in plants by modification of the techniques of Hiatt et al. (*Nature* 342, 76 (1989)) which have demonstrated the production of the immunoglobulin heavy and light chains in tobacco and other plants.

Techniques for the production of foreign proteins in the milk of transgenic animals have also been described in EPA 0264,166, fully incorporated herein. These techniques can readily be modified for production of CFTR in the milk of mammals. Similarly, the invention described herein enables the use of techniques known to those skilled in the art for the production of a transgenic animal model for cystic fibrosis. Such a CF animal model could be advantageously employed to screen for suitable pharmacological therapeutic agents as later described.

EXAMPLE 9

Characterization of the CFTR Protein
A. Isolation of CFTR.
CFTR is a membrane protein having an amino acid sequence which contains regions with extensive hydrophobic character. In order to purify CFTR as a functional protein it will be important to accomplish the solubilization of the CFTR from its native membrane such as through the use of detergents.

Conditions for the solubilization of CFTR from its natural lipid environment can be advantageously determined using whole cells, or membrane preparations prepared from cells which express CFTR. As will be readily understood, initial solubilization experiments will involve screening a variety of detergents at varying concentrations in order to find conditions that preferably achieve optimal solubilization of the CFTR. Briefly, packed membrane pellets are resuspended in detergent solution, gently homogenized, and the insoluble material removed by centrifugation at 100,000 g for one hour. The degree of solubilization achieved is ideally monitored immunologically. Potential detergents include but are not limited to, CHAPS (3-(3-cholamidopropyl) dimethylammonio)-1-pro(anesulfonate) (Borsotto M., et al., *J. Biol. Chem* 260. 14255 (1985)), Hamada and Tsuro, *J. Biol. Chem.* 263 1454 (1988)), n-octyl glucoside (Landry et al., *Science* 244, 1469 (1989)); lubrol (Smigel, *J. Biol. Chem.* 261, 1976 (1986)); Agnew et al., *Biochem. Biophys. Res. Comm.* 92, 860 (1980)); Triton X-100 (Hartshorne and Catterall, *J. Biol. Chem.* 259, 1667 (1984)); and Triton X-114 (Bordier, *J. Biol. Chem* 256, 1604 (1981)). The initial detergent solubilized CFTR solution can also be diluted into an appropriate concentration of detergent or detergent/lipid (Agnew and Raftery, *Biochemistry* 18, 1912 (1979)) to achieve stabilization of the CFTR. Compounds known to stabilize proper folding of membrane proteins, sometimes referred to as osmolytes, can also be used. Such stabilization agents include polyols such as Glycerol, sugars and amino acids (Ambudkar and Maloney, *J. Biol. Chem.* 261. 10079 (1986)). In addition, protease inhibitors against the four major classes of proteases are advantageously present throughout these procedures (Hartshorne and Catterall, *J. Biol. Chem.* 259. 1667 (1984)) and would include, for example, phenylmethylsulfonyl fluoride (PMSF) for serine proteases; iodoacetamide for thiol proteases; 1,10-phenanthroline for metalloproteases; and pepstatin A for proteases with activated carboxylic acid Groups. Ideally, studies should be carried out in which the concentrations are relative proportions of detergent, lipid and osmolyte are varied together with other buffer conditions in order to identify optimal conditions to preserve and stabilize the CFTR. For example, Agnew and Raftery varied the ratio of various detergents and lipids and determined that a 7 to 1 ratio of lubrol to phosphatidylcholine stabilized the solubilized voltage sensitive sodium channel for further purification. Similarly, Hartshorne and Catterall found that the presence of 0.25% egg phosphatidylcholine produced a more stable preparation and an increased recovery during purification to the sodium channel solubilized with Triton X-100. To determine the functional integrity of the solubilized protein may require reconstitution of the protein into liposomes using the procedure of Example 11, followed by introduction into cells and testing using the ion efflux assays of Example 14.

B. Immunoprecipitations and protein phosphorylation using protein kinase A.

The procedures employed for isotopic labeling of cells, preparation of cell lysates, immunoprecipitation of proteins and SDS-polyacrylamide gel electrophoresis were as described by Cheng et al., (1988) and Gregory et al., (1990). CFTR was phosphorylated in vitro with protein kinase A essentially as described by Kawata et al. (1989). Briefly, immunoprecipitates were incubated with 20 ng of protein kinase A (Sigma) and 10 μCi of ($\gamma^{32}$P)ATP in 50 μl of kinase buffer (50 mM Tris-HCl, pH 7.5, 10 mM $MgCl_2$ and 100 μg/ml bovine serum albumin) at 30° C. for 60 minutes. The reaction was stopped by the addition of 0.5 ml RIPA buffer (50 mM Tris-HCl, pH 7.5, 150 mM NaCl, 1% Triton X-100, 1% sodium deoxycholate and 0.1% sodium dodecyl sulphate). The procedure for Cleveland digestion was performed as described by Cleveland et al.,(1977) with modifications (Cheng et al., 1988).

C. Digestion with qlycosidases.

Figure 9:
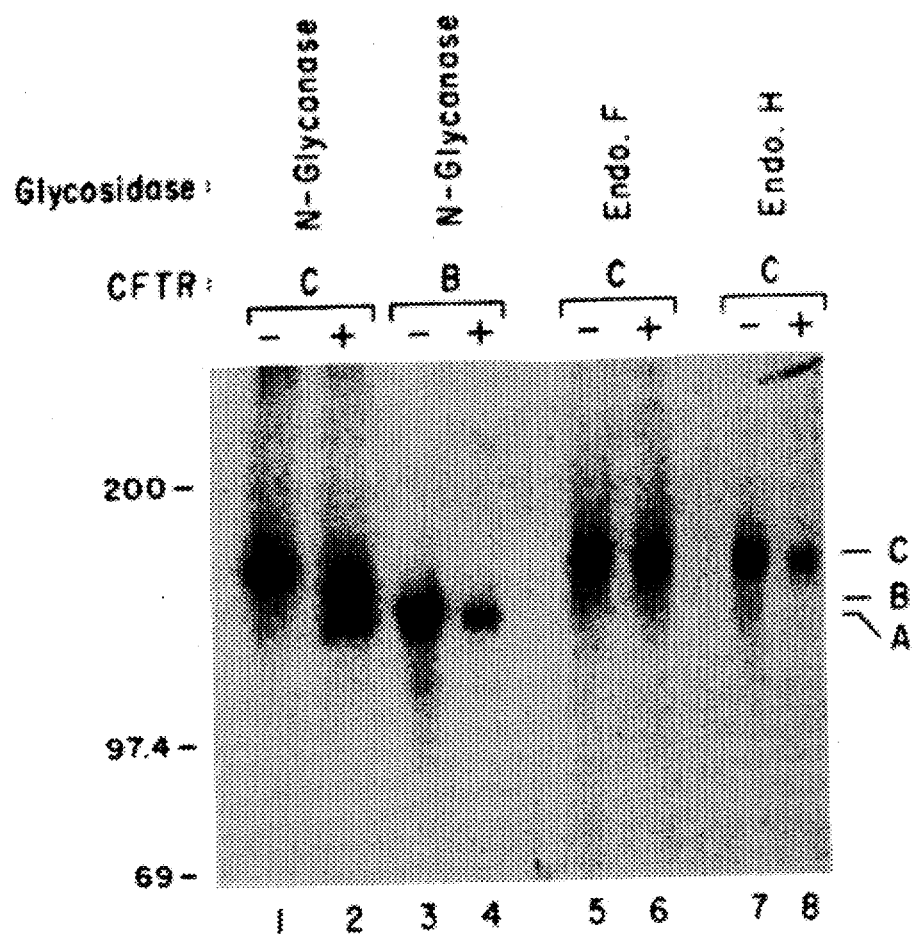
FIG. 9 shows treatment of CFTR with glycosidases.

The glycosidases N-GLYCANASE® enzyme, O-GLYCANASE® enzyme, endoglycosidase H and endoglycosidase F were obtained from Genzyme Corporation. Conditions for digestion with the respective enzymes were as specified by the manufacturer except incubations were performed at 37° C. for 4 h only. All digestions were performed on CFTR which had been purified by immunoprecipitation and separation on polyacrylamide gels (see Example 10). CFTR bands B and C were eluted from the gels by maceration of the gel pieces in extraction buffer (50 mM ammonium bicarbonate, 0.1% SDS and 0.2% β-mercaptoethanol). Referring to FIG. 9, bands B and C were immunoprecipitated from T84 cells and phosphorylated in vitro using protein kinase A and ($\gamma^{32}$P)ATP. The CFTR proteins were extracted from the SDS-polyacrylamide gels, subjected to no treatment (lanes 1, 3, 5 and 7) or were incubated with N-GLYCANASE® enzyme (lanes 2 and 4), endoglycosidase F (lane 6) or endoglycosidase H (lane 8). Samples were separated by electrophoresis and analyzed by autoradiography. Exposure was for 24 h.

D. Pulse-chase studies.

Figure 11A:
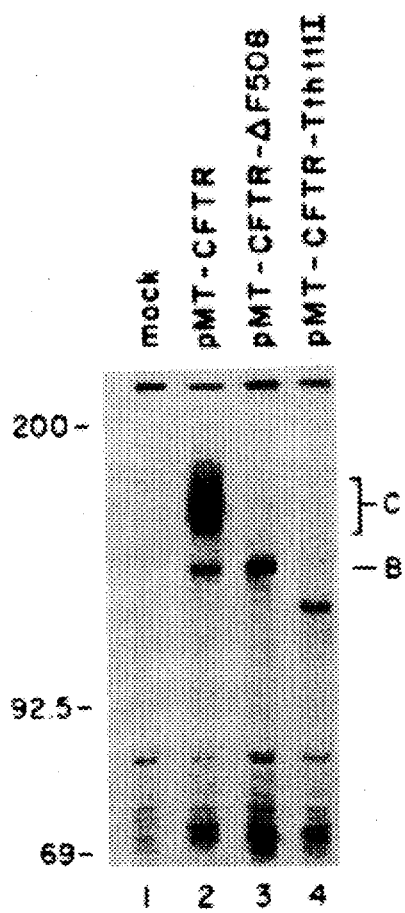
FIGS. 11A and 11B show pulse-chase labeling of wild type and ΔF508 mutant CFTR in COS-7 transfected cells.
Figure 11B:
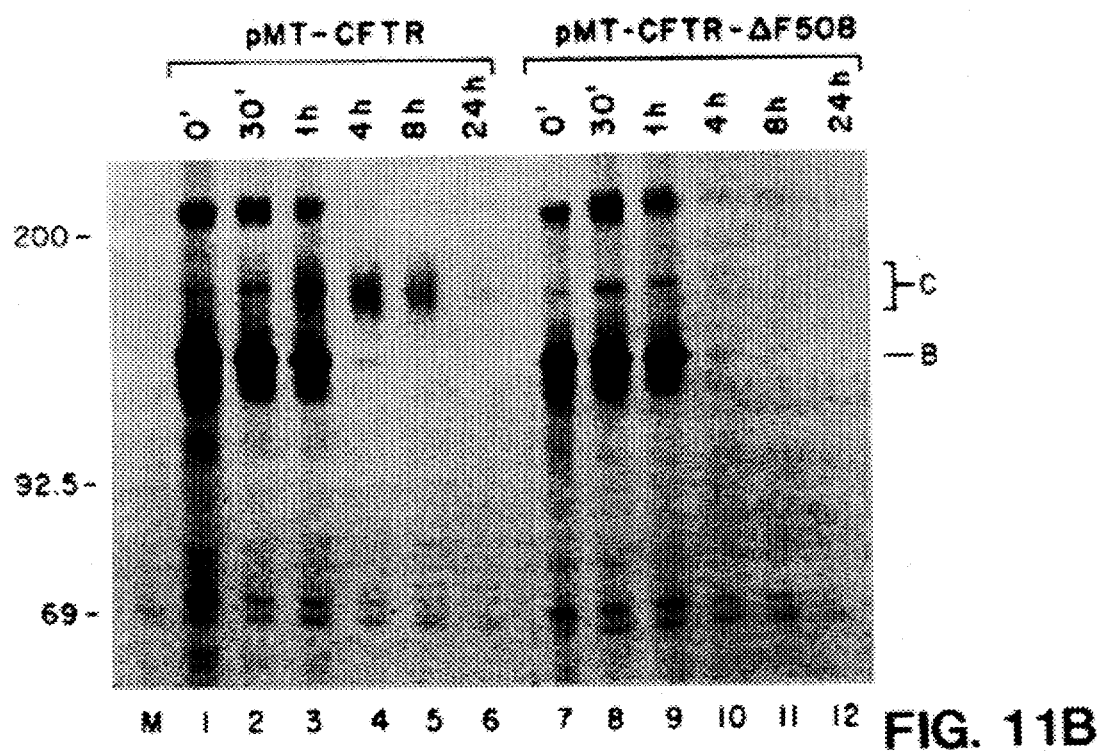
Figure 12A:
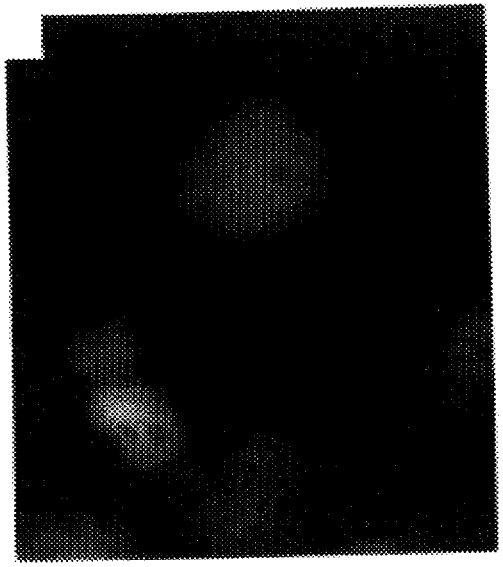
Figure 12B:
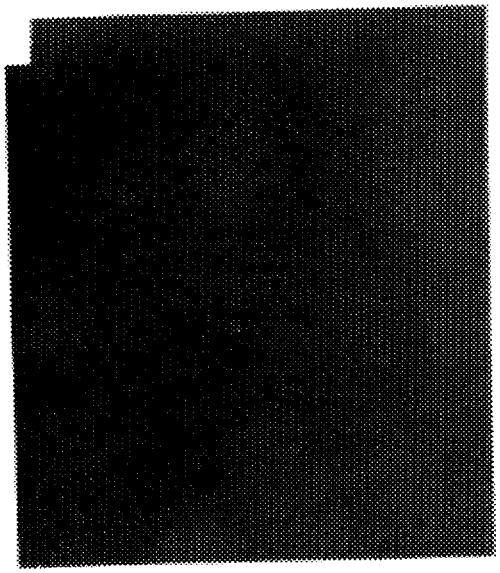
Figure 12C:
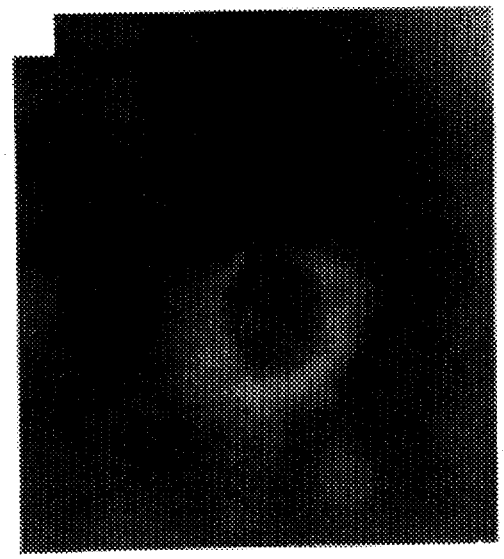
Figure 12D:

Six 90 mm dishes of COS-7 cells were transfected with either pMT-CFTR or pMT-CFTR-ΔF508. To avoid dish to dish variation in transfection efficiency, at 12 hours post-transfection, the cells were harvested by trypsinization and re-distributed among six 90 mm dishes. Following 18 h of incubation, the cells were washed twice with DME media (lacking methionine) and starved for 30 minutes at 37° C. $^{35}$S-methionine (250 μCi/ml) was then added to each dish and the plates labeled for 15 minutes at 37° C. At the end of the 15 minutes, the cells were washed twice with growth media, maintained in growth media and then chased for various times up to 24 h. Referring to FIG. 11A, COS-7 cells were mock transfected (lane 1) or transfected with pMT-CFTR (lane 2), pMT-CFTR-ΔF508 (lane 3) and pMT-CFTR-Tth 111 I (lane 4). 48 hours post-transfection, the cells were labeled for 12 h with $^{35}$S-methionine. CFTR from these lysates were immunoprecipitated with the monoclonal antibody mAb 13.1 (see Example 11) and then analyzed on an SDS-polyacrylamide gel. The gel was fluorographed and exposed for 4 h. In FIG. 11B COS-7 cells were either transfected with pMT-CFTR (lanes 1–6) or pMT-CFTR-ΔF508 (lanes 7–12). At 48 h post-transfection, the cells were labeled for 15 minutes with $^{35}$S-methionine. After being labeled, the cells were either harvested immediately or rinsed several times with labeling media, transferred to a standard growth media and then harvested at various times thereafter. The lysates prepared were immunoprecipitated with mAb 13.1 and analyzed on an SDS-polyacrylamide gel. The fluorograph gel was exposed for 6 hours.

E. Immunofluorescence microscopy.

Indirect immunofluorescence was performed essentially as described by Kalderon et al. (1985). COS-7 cells which had been transfected with CFTR-containing cDNAs (see Example 7) were transferred onto glass coverslips at 12 h. Following a further 18 h incubation at 37° C., the cells were fixed in 3.7% formaldehyde in phosphate buffered saline (30 minutes at room temperature), permeabilized with 1% Nonidet P40 (15 minutes at room temperature) and incubated with the monoclonal antibody mAb 13.1 (see Example 11) followed by FITC-conjugated goat anti-mouse IgG (Cappel Labs.). The coverslips were mounted using 50% glycerol in phosphate buffered saline and viewed using a Zeiss Axiopian microscope. With reference to FIG. 12, 48 hours after transfection, the cells were fixed and stained using the monoclonal antibody mAb 13.1 (Example 11) or 423 (specific for SV40 Large-T antigen) as first antibody. The second antibody was fluorescein-conjugated goat anti-mouse IgG. The localization of the various CFTR proteins were visualized by immunofluorescence microscopy. Micrograph (A) shows nuclear staining of SV40 Large-T antigen using the monoclonal antibody 423 (Harlow et al., 1981); (B) shows pMT-CFTR incubated with mAb 13.1 in the presence of excess fusion protein; (C) shows pMT-CFTR-ΔF508 incubated with mAb 13.1 and (D) shows pMT-CFTR incubated with mAb 13.1.

EXAMPLE 10

Purification of the CFTR Protein

Utilizing the solubilized CFTR protein from Example 9, one may purify the CFTR utilizing purification procedures which have been employed previously with similar membrane proteins. Although proteins with multiple membrane spanning domains have been purified using conventional techniques (Catterall, *Science* 242 50 (1988)), the generation of specific antibodies has allowed other investigators to develop rapid and simple purification schemes for P-glycoprotein (Hamada and Tsuro, *J. Biol. Chem.* 263 1454 (1988)), and sodium channels (Casadei et al., *J. Biol. Chem.* 261 4318 (1986)); Nakayamo et al.,*Proc. Natl. Acad. Sci.* 79 7575 (1982)). Thus, the production of CFTR specific antibodies (see Example 11) could facilitate the purification of the CFTR molecule and allow its purification away from the relatively high level of contaminants expected in the starting solubilized preparation.

For example, antibodies produced against an extracellular or other domain of the CFTR could be screened to select therefrom an antibody having a suitably high binding coefficient appropriate for use in the purification scheme. The selected antibody is ideally immobilized on a variety of commercially available resins including CNBr activated Sepharose, Affi-Gel 10, Reacti-Gel CDI and Amino-Link resins and tested for immobilized antibody capacity. Optimal conditions for binding CFTR to the column, washing the column to remove contaminants, and eluting the purified protein can then be determined using conventional parameters as the starting point and testing the effect of varying the parameters. It will be recognized that effective wash and elution conditions will significantly impact the degree of purification obtained. Extensive washing in the presence of stabilizers plus higher salt and differing detergents may be utilized to remove nonspecifically absorbed proteins. Elution may then be advantageously carried out either using specific peptide elution if one has antibodies to CFTR peptides. (Courtneige et al., *Cold Spring Harbor Conf. on Cell Prolif. and Cancer* 2 123 (1984)), or alternatively by chaotropic agents such as potassium thiocyanate or by lowering the pH followed by immediate pH neutralization of the eluted fractions.

Although it is likely that immunoaffinity chromatography would provide a significant purification and provide protein of sufficient purity for research studies and drug screening, such an approach alone may not provide adequate protein purity to qualify the CFTR protein as a clinical grade therapeutic agent. Thus, to purify the protein further or in the case that immunoaffinity chromatography was unsuccessful, one could evaluate additional chromatographic approaches to select an optimal chromatography procedure to obtain the desired purity. For example, ligand affinity (Landry et al., *Science* 244 1469 (1989); Smigel, *J.Biol.Chem.* 261 1976 (1986)), lectin (Curtis and Catteral, *Biochemistry* 23 2113 (1984)), anion exchange (Hartshorne and Catteral, *Proc. Natl Acad. Sci.* 78 4620 (1981)), hydroxylapatite (Hartshorne and Catteral, *J.Biol.Chem.* 259 1667 (1984)), and gel filtration (Borsotto et al., *J.Biol.Chem,* 260 14255 (1985)) chromatography procedures have been used in purification schemes for this class of membrane bound proteins. Since the CFTR protein contains a nucleotide binding domain, it will likely bind to resins such as Cibicron blue and may be specifically eluted with nucleotides (Lowe and Pearson, *Methods in Enzymology* 104 97 (1984)). The accessibility of the nucleotide binding domain in the solubilized form would have to be determined empirically. The predicted protein sequence for the CFTR contains a carbohydrate attachment site at amino acid 894. Since it has now been shown that the CFTR protein is a glycoprotein, the use of lectin chromatography is a likely route to purify CFTR.

EXAMPLE 11

Preparation of CFTR Protein Specific Antibodies

Monoclonal antibodies mAb 13.1 and mAb 13.2, specific for predetermined regions or epitopes of the CFTR protein, were prepared using the following cloning and cell fusion technique. A mouse was immunized with the polypeptide produced from Exon 13 of the CFTR protein fused to galactosidase, the fusion protein being obtained as described in Mole and Lane, *DNA Cloning Volume III: A Practical Approach* (1987), to induce an immune response. The immunization procedure required injecting a mouse with 10 µg of immunogen in 10 µl of PBS emulsified in 30 µl of Freund's complete adjuvant (Gibco #660-5721AS). This procedure was repeated four times at intervals of from 1 to 28 days over a 57 day period. The mouse was then injected with 50 µg of immunogen in 50 µl of PBS four times over a three day period. Vasodilation was induced by warming the mouse for 10 minutes with a desk lamp. The mouse was sacrificed by $CO_2$ intoxication and a splenectomy was performed.

After immunization was carried out, the β-lymphocytes of the immunized mice were extracted from the spleen and fused with myeloma cells using the well known processes of Koehler and Milstein (*Nature*, 256 495–497 (1975)) and Harlow and Lane (*Antibodies, A Laboratory Manual*, Cold Spring Harbor Laboratory, New York (1988)), respectively. The resulting hybrid cells were cloned in the conventional manner, e.g., using limiting dilution, and the resulting clones, which produce the desired monoclonal antibodies, cultured. Two most preferred antibodies produced by this process were mAb 13.1 and mAb 13.2, specific for Exon 13.

The monoclonal antibodies, mAb 13.1 and mAb 13.2, may be used in their complete form or as fragments thereof (e.g., Fab or F(ab')$_2$ fragments) providing they exhibit the desired immunological reactivity with CFTR or the desired CFTR domain. The term "monoclonal antibody" as used herein therefore also includes such fragments. The monoclonal antibody is ideally used in an immobilized form, and is most preferably immobilized on a resin substrate, for purification of the CFTR protein from other contaminants. The antibodies can also be advantageously used as part of a kit to assay for the presence of the CFTR protein in biological samples such as fluids or on the surface of cells.

Hybridomas producing monoclonal antibodies mAb 13.1 and mAb 13.2 prepared according to this procedure have been deposited with the American Type Culture Collection (ATCC) under the terms of the Budapest Treaty, and assigned accession numbers: ATCC 10565 and ATCC 10566, respectively.

EXAMPLE 12

CFTR Production Results from Cells Transformed with Various CFTR genes including Mutants A. CFTR from T84 cells.

Previous examples show that CFTR can be detected in T84 cells by adding ($\gamma^{32}$P)ATP and protein kinase A to immunoprecipitates formed using antibodies raised against CFTR (see also Gregory et al., 1990). Band B, and large amounts of band C were detected by this method (see FIG. 9). Partial proteolysis fingerprinting showed that the T84 cell-derived material and that produced in a cell-free system directed by CFTR RNA were indistinguishable.

FIG. 9 demonstrates that band C is CFTR modified by addition of N-linked carbohydrate. Upon treatment with N-GLYCANASE® enzyme, band C, immunoprecipitated from T84 cells and phosphorylated in vitro, is converted to band A. Treatment with O-GLYCANASE® enzyme, endoglycosidase H or endoglycosidase F enzymes had no effect (FIG. 9). Because a band of intermediate molecular weight was also detected upon treatment with N-GLYCANASE® enzyme, these results can be interpreted to mean that CFTR bears two complex carbohydrate side chains possibly of the tri- or tetra-antennary type. N-GLYCANASE® enzyme treatment of band B also yielded band A (FIG. 9) (see also Gregory et al., 1990). The shift in apparent molecular weight on polyacrylamide gels in going from band A to band C seems large (20K) but whether this represents addition of unusually large side chains, or merely results from anomalous migration in SDS-polyacrylamide gels is unknown. It is postulated that glycosylation of band C is probably also responsible for its migration as a diffuse band as opposed to the sharp appearance of bands A and B.

B. ΔF508 does not Produce Mature CFTR.

Figure 10A:
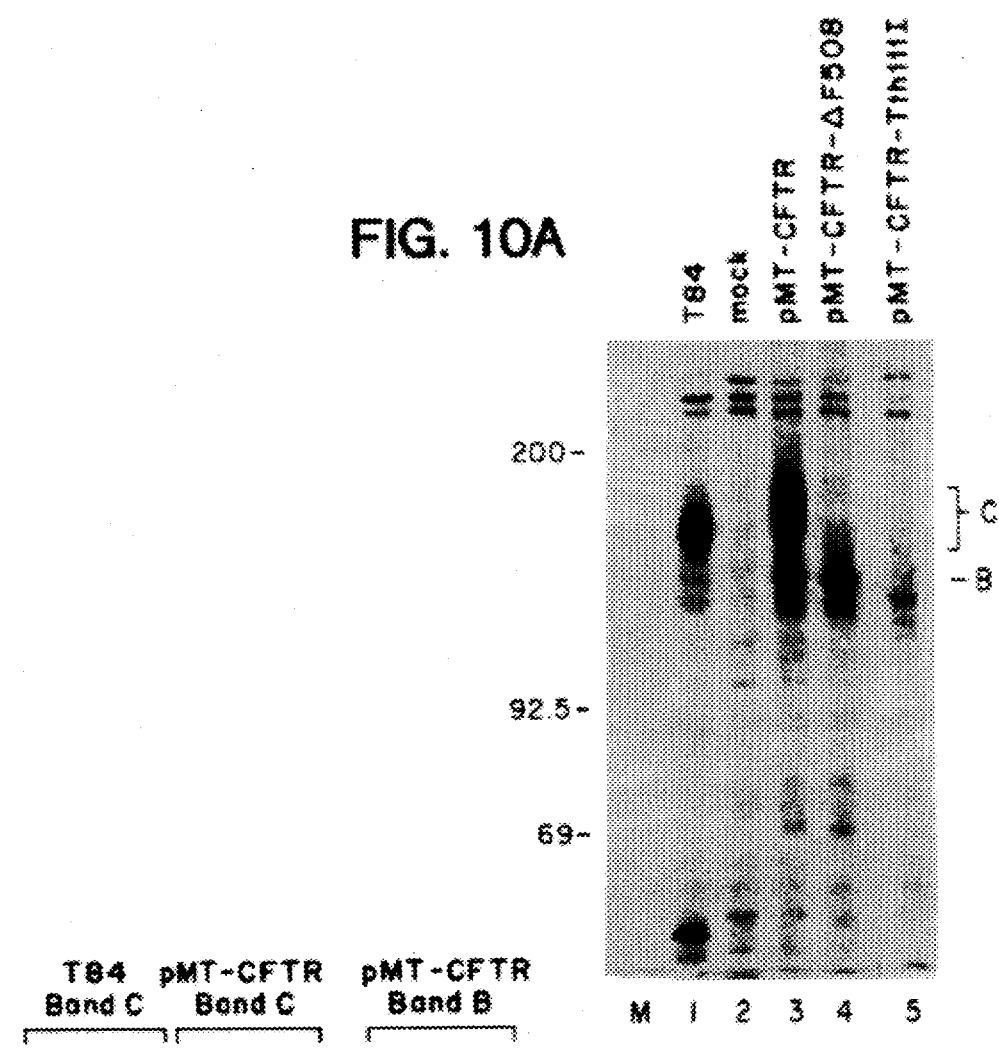
FIGS. 10A and 10B show an analysis of CFTR expressed from COS-7 transfected cells.
Figure 10B:
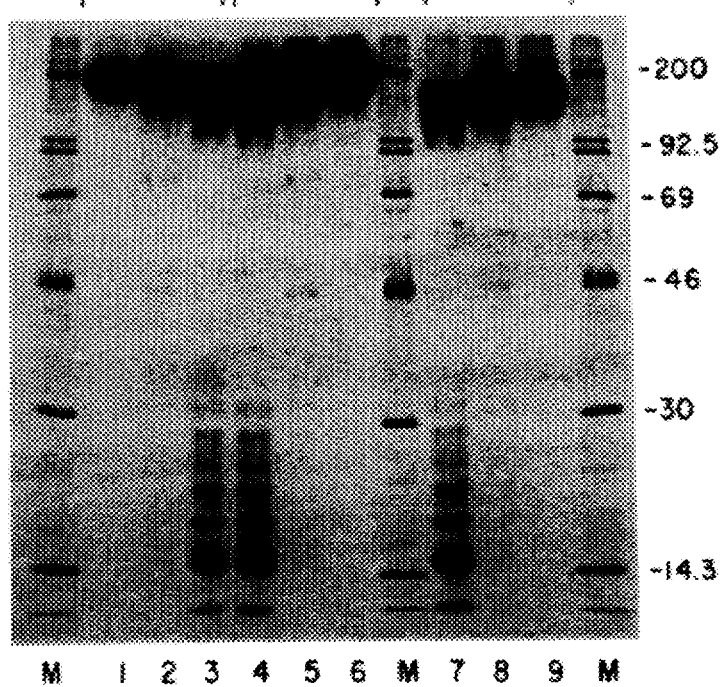

Recombinant CFTR has been expressed utilizing a vaccinia virus-infected HeLa cell system (see also Gregory et al., 1990; and Rich et al., 1990). Because of the short infection cycle of vaccinia virus, longer term expression was studied in transfected COS-7 cells (see Example 7). With reference to FIG. 10A, COS-7 cells were either mock transfected (lane 2), transfected with wild-type CFTR (pMT-CFTR-lane 3) or the mutants pMT-CFTR-ΔF508(lane 4) and pMT-CFTR-Tth111 (lane 5). Lysates were prepared 48h post-transfection, phosphorylated in vitro with protein kinase A and ($\gamma^{32}$P)ATP and analyzed on a SDS-polyacrylamide gel. Lane 1 contains lysate from T84 cells. The positions of bands B and C are indicated on the right margin. Autoradiography was for 2 h. With reference to FIG. 10B, the 32p in vitro labeled bands C from T84 cells (lanes 1–3) and from COS-7 cells transfected with pMT-CFTR (lanes 4–6) and band B from cells transfected pMT-CFTR (lanes 7–9) were excised from the gel and digested with increasing amounts of *S. aureus* V8 protease. Proteins in lanes 2, 5 and 8 were digested with 0.017 µg/µl of *S. aureus* V8 protease and those in lanes 3, 4 and 7 with 0.17 µg/µl of enzyme. Lanes 1, 6 and 9 were untreated samples. Exposure time was two days.

Thus, FIG. 10A shows CFTR produced in cells transfected with an expression plasmid (pMT-CFTR) containing a full length CFTR coding sequence expressed from a mouse metallothionein promoter. Using the $^{32}$p in vitro labeling technique and affinity purified polyclonal antibody (pAb Ex13) to exon 13 fusion protein (see also Examples 10, 11, 15 and also Gregory et al., 1990), band C was readily detected in transfected cells, as well as smaller amounts of band B (lane 3). COS-7 cell band C migrated more slowly than the CFTR from T84 cells (lane 1) but FIG. 10B shows partial proteolysis fingerprints that confirm that the proteins are indeed related. Presumably, the glycosylation pattern of human colon and simian kidney cells is sufficiently different to alter the mobility of band C.

FIG. 10A also shows that COS-7 cells transfected with vectors containing a ΔF508 cDNA produced band B but, unexpectedly, they did not contain band C (lane 4). Similarly, a mutant CFTR truncated by insertion of a frame shift mutation at the Tth111 I site (which resulted in the synthesis of a 1357 amino acid protein) encoded a truncated version of band B of predicted molecular weight but also lacked the band C equivalent (lane 5).

To confirm this data, metabolically labeled COS-7 cells were used. After the cells were labeled with $^{35}$S-methionine for 16 hours, they were lysed and immunoprecipitated with monoclonal antibody mAb 13.1 (raised against exon 13 fusion protein)(see Example 11). FIG. 11A shows that band B was labeled in COS-7 cells transfected with wild-type (lane 2) and ΔF508 cDNA (lane 3) but surprisingly, that labeled band C was totally absent in the mutant of cDNA transfected cells.

FIG. 11B shows the result of a pulse-chase experiment in which COS-7 cells, transfected with wild-type and ΔF508 cDNA vectors pursuant to Example 7, were labeled for 15 mins. and chased over a 24 hour period. Wild-type band B chased into band C such that by 4 hours after labeling, very little band B remains (lane 4). Mature CFTR was observed at 1, 4 and 8 h post labeling but by 24 hours, little remaining labeled material was detected. By contrast, although ΔF508 was metabolized with approximately the same half-life as wild-type, no band C appeared.

Not all labeled band B in pulse labeled wild-type cDNA transfected cells appeared to be processed to the fully glycosylated band C. One interpretation of this finding is that recombinant cells contained such large amounts of CFTR that the machinery responsible for further post-translational processing was saturated. Under these circumstances, excess material may be degraded. An alternative explanation is that during the chase period, so much unlabeled CFTR accumulated that insufficient antibody was present to capture all the labeled protein. Studies with vaccinia virus-infected HeLa cells synthesizing CFTR showed that very little band C material was detected in a 1 h labeling period. This labeling pattern is consistent with the kinetics shown here.

C. Immunofluorescence Studies.

The absence of mature CFTR in ΔF508 cDNA transfected-COS-7 cells implies that the deletion caused a structural alteration that somehow prevented maturation of the carbohydrate in the Golgi. This could result because transport from the endoplasmic reticulum to the Golgi was inhibited or because modification was inhibited even though transport was normal. It was hypothesized that if protein transport were inhibited it might be possible to detect a difference in location of mutant and wild-type recombinant CFTR by immunofluorescence.

FIG. 12 shows immunofluorescence photomicrographs of COS-7 cells transfected with wild-type and ΔF508 CFTR cDNAs using monoclonal antibody mAb 13.1. That the fluorescence detected was CFTR is indicated by the previous characterization of the monoclonal antibody, by the absence of signal in non-transfected cells (background cells in FIGS. 12 c and 12d) and because the reaction was inhibited by exon 13 fusion protein (FIG. 12b) but not irrelevant fusion protein. FIGS. 12c and 12d show that the subcellular distribution of wild-type and ΔF508 CFTR was different. The ΔF508 signal appeared localized to the perinuclear region whereas the wild-type CFTR signal was more diffuse. The pattern observed with wild-type suggests a widespread distribution possibly including the plasma membrane.

Because the distribution of CFTR in recombinant cells overexpressing the protein may not be typical, subcellular localization of wild-type and ΔF508 was not refined. Subcellular distribution of ΔF508 CFTR was different from wild-type.

D. Other Mutations Prevent Maturation of CFTR.

To study the maturation of CFTR in more detail, additional site specific mutations within the cDNA coding sequence were constructed. A naturally occurring deletion mutation at residue 507 was created by removing the codon for isoleucine (Kerem et al., 1990). To examine the role of nucleotide binding within the domain including ΔF508, the highly conserved lysine at residue 464 (Riordan et al., 1989) was then changed to methionine. The equivalent mutation was also made within the second nucleotide binding domain (K1250M) and both asparagine residues (at 894 and 900) were changed to glutamine to which carbohydrate is predicted to be attached (N894,900Q) (Riordan et al., 1989).

Vectors containing each of these mutations were constructed and separately transfected into COS-7 cells. With reference to FIG. 13, expression vectors containing wild-type CFTR pMT-CFTR (lane 2) and those containing the mutants pMT-CFTR-K464M (lane 3), pMT-CFTR-K1250M (lane 4), pMT-CFTR-ΔI507 (lane 5), pMT-CFTR-N894, 900Q (lane 6, marked as pMT-CFTR-deglycos.) and pMT-CFTR-R334W (lane 7) were transfected into COS-7 cells. Lane 1 is COS-7 cells which had been mock transfected. Lysates were prepared 48 h post-transfection and the immunoprecipitates formed using pAb Ex13 were labeled in vitro using protein kinase A and ($\gamma^{32}$P)ATP. The positions of bands A, B and C are indicated on the right margin. Autoradiography was for 2 h.

FIG. 13 shows that using the in vitro kinase assay, ΔI507 cDNA transfected cells, like their ΔF508 counterparts, lacked band C (lane 5). N894,900Q produced neither band B or C, but instead yielded a band of slightly increased mobility which was interpreted to be the CFTR primary translation product, band A, of apparent molecular weight 130kd (lane 6). This confirmed that it was the addition of N-linked carbohydrate to CFTR that caused the mobility shifts resulting in bands B and C. Individual mutations in each of the two sites was required to establish unequivocally that both Asn894 and Asn900 are glycosylated and based on the N-GLYCANASE® enzyme results, this seems likely.

K464M cDNA transfected cells, like their ΔI507 and ΔF508 nucleotide binding domain 1 mutant counterparts, contained no band C (lane 3). Surprisingly, however, the equivalent mutation in the conserved lysine of the second nucleotide binding domain did not prevent maturation (lane 4). Another rare but naturally occurring mutation associated with CF occurs at residue Arg334 within transmembrane domain 6. This mutation R334W, did not prevent maturation of recombinant CFTR band C, (lane 7).

Table 2 summarizes data obtained with all the mutants including two other naturally occurring CF associated mutations S5491 and G551D. These were from a second cluster of mutations within the first nucleotide binding domain, in this case within exon 11 (Cutting et al., 1990a; Kerem et al., 1990). Also included is F508R, in which the residue at 508 was changed rather than deleted. Surprisingly, the results using these mutants showed S5491 CFTR does not mature but G551D does. The mutation of phenylalanine 508 to arginine also resulted in CFTR that did not mature.

EXAMPLE 13

Intracellular Characterization of CFTR

A. Endoplasmic reticulum interactions.

Based on the discoveries of this invention, nascent CFTR interacts first with the endoplasmic reticulum and is then glycosylated at least one of Asn residues 894 and 900. The native molecule is then transported to the Golgi where carbohydrate processing to complex-type glycosylation occurs. Finally, at least some of the mature glycosylated molecule is thereafter transported to the plasma membrane.

It is now reasonably well established that the endoplasmic reticulum possesses a mechanism that prevents transport of mutant, misfolded or incorrectly complexed versions of proteins otherwise destined for further processing (Lodish, 1988; Rose and Doms, 1988; Pelham, 1989; Hurtley and Helenius, 1989; Klausner and Sitia, 1990). If this quality control mechanism operates on CFTR, it would prevent transport to the Golgi and consequently, further modification of several of the mutants reported here. As a result, the unmodified mutant versions of the protein either would not exit the endoplasmic reticulum and would subsequently be degraded therein, or alternatively, they would be transported to the lysosomes for degradation.

It is not clear how the quality control mechanism recognizes the difference between wild-type and those mutant versions of CFTR which were not further processed. One obvious mechanism would be that an alteration in structure of the molecule is detected. Indeed, gross changes in structure of the first nucleotide binding domain (and perhaps in consequence of the whole molecule) might be expected following deletion of phenylalanine 508 (Hyde et al., 1990). However, it is not clear how this change in structure would be detected by a mechanism located, for example, in the lumen of the endoplasmic reticulum, since the domain bearing the mutation, would lie on the cytosolic side of the membrane. Perhaps the structural change is transmitted across the membrane or perhaps the sensing mechanism does not recognize CFTR directly, but rather detects a protein with which it is complexed. In this case, all mutations within CFTR that prevent complex formation also prevent intracellular transport. Yet another mechanism would be that nascent CFTR has basal activity in the endoplasmic reticulum and that mutations that disrupt this activity are sensed by the quality control mechanism. Perhaps some activity of CFTR is necessary for its maturation and by this means, enzymatically inactive proteins are marked for degradation. Irrespective of the mechanism of discrimination, the time course of synthesis of both wild-type and mutant CFTR is notable in two respects. Firstly, the half life of band B is similar for both wild-type and mutant versions and secondly, most of the wild-type band B appears to be degraded. One interpretation of these results is that synthesis of CFTR involves two steps, retention in the endoplasmic reticulum during which time folding of the protein occurs followed by either export to the Golgi or degradation. Since we detect no difference in the residence time in the endoplasmic reticulum, it would appear that the defect in the case of the non-maturing mutants lies in the second step, that which results in degradation. Furthermore, even wild-type seems surprisingly susceptible to degradation since most of band B fails to mature to band C. Whether this results from overexpression of CFTR or is a property of the protein in non-recombinant cells remains to be determined.

Still alternatively, the CFTR protein itself may be responsible for its own exportation out of the endoplasmic reticulum. Under this interpretation, mutant CFTR, or otherwise improperly folded or glycosylated CFTR would not appropriately interact with the endoplasmic reticulum membrane resulting in a self-regulating quality control mechanism having no need of further structures or accessory substances.

A different interpretation of the results would provide that the nascent, incompletely glycosylated CFTR was transported normally to the Golgi but that the structural alterations caused by the various mutations prevented further glycosylation and this lead to lack of activity and eventual degradation. This interpretation is less favored because the previous explanations are more consistent with the present understanding of the intracellular transport of other proteins and their mutant variants (Lodish, 1988; Pelham, 1989; Klausner and Sitia, 1990).

B. Structure: Function of CFTR.

CFTR is a large, complex molecule. Nucleotide binding domain 1 contains two clusters of naturally occurring mutations, one around residue 508 (Riordan et al., 1989; Kerem et al., 1990), the other around 550 (Cutting et al., 1990a; Kerem et al., 1990). All the mutations around 508 disclosed herein (ΔF508, ΔI507, F508R) failed to generate mature CFTR, whereas mutations at the second site, S549I did not produce mature CFTR but G551D did. Mutation of the Walker motif lysine in nucleotide binding domain 1 also prevented maturation of CFTR. The difference between mutations at neighboring residues 549 and 551 is a surprising result. It appears that most of these mutations inactivate some function of the protein, such as its ability to bind nucleotide and maturation of CFTR is prevented by lack of functional activity. More likely, all non-maturing mutants result in structural changes in the domain and these prevent maturation.

Another unexpected result of the experiments disclosed herein is the difference between the modification of the conserved lysine mutants in nucleotide binding domains 1 and 2. K464M did not produce mature CFTR whereas K1250M did. Although the two domains are clearly related and both mutations lie in putative nucleotide binding pockets (Riordan et al., 1990), they appear not to be functionally equivalent.

Mutant R334W emphasized the importance of the transmembrane domains in the activity of CFTR. The instant disclosure clearly shows that a change in sequence within transmembrane domain 6 does not prevent movement to the Golgi at least as measured by the presence of complex-type N-linked oligosaccharides. Accordingly, the polar amino acid in the otherwise hydrophobic environment plays an important role in pumping material across the membrane.

EXAMPLE 14

Cystic Fibrosis Disease Implications—Diagnosis and Therapy

A. Molecular basis of the disease.

Many genetic diseases are caused by the absence or truncation of the appropriate protein, for example as a result of deletions within the corresponding gene. Muscular dystrophy would be an example in this category (Harper, 1989). Other genetic diseases are caused by mutations that result in loss of function of the gene product. Sickle cell disease is a classic example of this type (Weatherall.et al., 1989). One aspect of the instant invention provides that the molecular basis of most cystic fibrosis is the inability of the CFTR gene product to mature. That is to say, the failure of CFTR to move through the normal pathway of intracellular trafficking and modification means that the mature protein is absent from its final cellular destination in CF cells. Examples of genetic lesions that result in failure of the LDL receptor to mature have been described for certain types of familial hypercholesterolemia. In some of these cases, the mutant LDL receptor is retained in the endoplasmic reticulum (Lehrman et al., 1986).

That little or no mature CFTR has been detected in the cells containing CF associated mutations observed in a majority of CF patients does not necessarily mean that this forms the molecular basis of all CF. A priori, it seems very likely that some mutations will inactivate the function of CFTR but will not prevent transport and glycosylation. Indeed, R334W and G551D have been detected in CF chromosomes and presumably encoded inactive CFTR (Kerem et al., 1990). Even so, both encoded CFTR that matures to form band C.

B. Diagnosis.

The mutations described herein represent over 70% of known CF chromosomes (Kerem et al., 1989, 1990; Riordan et al., 1989; Cutting et al., 1990a). Accordingly, the surprising results of the instant invention can be used for purposes of diagnosing CF. Further, it is anticipated that mutations in other CF chromosomes will also fail to produce band C, thus making the detection of CFTR protein in the membrane diagnostic of an even greater percentage of CF. Another aspect of the present invention is the diagnosis of CF by monitoring the presence or absence of mature CFTR. Accordingly, the sensitive detection of band C in primary cells provides a surprisingly useful diagnostic test for detecting the great majority of CF patients.

C. Pancreatic sufficiency and insufficiency.

To date some mutations that cause premature termination of CFTR synthesis appear associated with mild forms of CF, whereas ΔF508 is often associated with severe, pancreatic insufficient forms of the disease (Cutting et al., 1990b) That ΔF508 should be more severe than a major truncation appears counter intuitive. The experimental data disclosed herein support the conclusion that major truncations make no stable CFTR. By contrast, homozygous ΔF508 cells not only make no mature CFTR but worse, they produce mutant protein trapped in the endoplasmic reticulum. Trapped ΔF508 CFTR may retain sufficient activity to cause intracellular pumping of molecules normally transported only at the cell surface. Thus, CFTR activity at the incorrect cellular location would result in effects more serious than those resulting from complete absence of the protein. Accordingly, suitable therapeutic activity would ideally deactivate such inappropriate CFTR activity most preferably, in advance of, or in conjunction with CFTR protein or CFTR gene therapy.

D. Recessive nature of CF.

The absence of mature CFTR encoded by ΔF508 and other similar mutants also provides an explanation for the finding that cells heterozygous for various mutations are apparently wild-type in cell surface channel activities associated with CFTR. Previously, it was perhaps surprising that the defective molecule did not interfere with the activity of the wild-type. From the instant invention, it was surprisingly discovered that cells heterozygous for ΔF508 completely lack mutant CFTR at the cell surface and in consequence, the wild-type protein is able to function uninterrupted.

E. Therapy.

The instant discovery that the majority of cases of CF are caused by the absence of mature CFTR and possibly, in the case of pancreatic insufficiency, by the additional deleterious effects of incorrectly located, partially active CFTR, confirms the basis of other approaches to CF therapy. For example, drugs active in altering the subcellular distribution of proteins could advantageously be used to redistribute to the plasma membrane mutant forms which retain at least some functional activity. Similarly, agents effective in stimulating sufficient CFTR activity to result in export of otherwise mutant CFTR to the Golgi for additional glycosylation could result in improved CFTR function in homozygous CF individuals. Alternatively, therapeutic treatment via a suitable, therapeutically effective blocking agent could be used to deactivate inappropriately located, active, mutant CFTR protein. Alternately, one may promote the transport of such protein to an appropriate location and useful in this regard are reagents active in promoting intracellular transport inhibition. Yet another aspect of the present invention regarding the therapeutic treatment of mislocated CFTR comprises the use of antisense nucleic acid to rid cells of mutant transcript to provide the absence of CFTR which is preferable to incorrectly located protein.

Most preferably, treatment of individuals with CF will comprise the administration of a therapeutically effective amount of replacement CFTR protein. Ideally, the CFTR will be administered via aerosol inhalation so that it is applied directly to the airway cells. The CFTR protein could be formulated in a lipid containing vehicle such as liposomes or in virosomes. The final formulation will advantageously comprise a carrier as a vehicle for physically transporting the CFTR and also ideally chemically stabilizing the CFTR. The most preferred embodiment will also comprise a dissolving agent for dissolving the mucous or otherwise assisting the movement of the CFTR through the mucous layer to the airway cellular membrane. Ideal reagents in this regard would target the CFTR and/or the delivery vehicle to airways cells and further, promote fusion therewith. Reagents active in this manner include viral proteins such as the HA protein (for targeting) and F protein (for fusion) of parainfluenza viruses.

EXAMPLE 15

Effect of Temperature on Processing of CFTRΔF508 and Wild-Type CFTR

3T3 fibroblasts expressing CFTR and CFTR Δ508 were generated as described in Berger H. A. et al., *J. Clin. Invest.* 1422–1431 (1991). Cells were seeded on 100 mm culture dishes and grown to 50–70% confluence. Cultures were then grown either at 37° C., 30° C., 26° C. or 23° C. for 2 days. At the end of the incubation period, cultures were washed twice with phosphate buffered saline and solubilized for 30 minutes at 4° C. with lysis buffer (150 mM NaCl, 50 mM Tris, pH 7.5, aprotinin at 1 μg/ml$^{-2}$ and 1 mM PMSF) containing 1% recrystallized digitonin. Equal amounts of starting protein (1.2–1.4mg per sample) were immunoprecipitated with monoclonal antibody mab 13.1 and phosphorylated with ($\Delta^{32}$p) ATP and the catalytic subunit of PKA as described in Cheng, et al. *Cell* 83:827–834 (1990). Proteins were separated on 6% SDS-polyacrylamide gels and prepared for autoradiography. Quantitative assessment of radioactivity in gels and subtraction of background was done using a radioanalytic imaging system (AMBIS, San Diego). To avoid problems inherent in attempts to quantify absolute amounts of protein by immunoprecipitation, data is presented as a percentage of total CFTR in band C.

The results of the study, which are presented in FIG. 14, indicate that percentage of mature CFTR produced from CFTRΔF508 increases upon exposure to reduced temperatures.

A. Time-dependence and Reversibility of Incubation at a Reduced Temperature.

3T3 fibroblasts expressing CFTRΔF508 were grown for 6, 12, 24, 48, 72 and 96 hours at 26° C. An autoradiograph of a 6% SDS polyacrylamide gel showed that as the length of incubation at a 26° was increased, the percent of CFTRΔF508 present in the fully glycosylated form progressively increased.

3T3 fibroblasts expressing CFTRΔF508 were grown for two days at 26° C. and then grown at 37° C. for 0 hrs., 2 hrs., 4 hrs., 6 hrs., 12 hrs., or 24 hrs. An autoradiograph of a 6% SDS polyacrylamide gel showed that the amount of mutant protein present as band C decreased with a half-life of about 7 hrs.

B. Effect of Temperature on Processing Efficiency of CFTRΔF508.

C127 cells (a cell line of mouse mammary epithelial origin) expressing CFTR or CFTRΔF508 were generated by calcium phosphate-mediated transfection with a bovine papilloma virus-based vector containing CFTR cDNA under control of the mouse metallothionein MT1 promoter and a neomycin-resistance gene (as the selectable marker) under the control of another copy of MT1 promoter. Pulse-chase experiments were performed and assayed as described (Cheng, et al. Cell 83 (1990)), except that CDIM (carbon dioxide-independent medium; Gibco) was used for the chase, and the monoclonal antibody (24–1) was directed against a carboxy-terminal epitope. Under these conditions (100 μl of hybridoma supernatant and an overnight incubation) CFTR was maximally, immunoadsorbed, so no additional CFTR was recovered after immunoprecipitation with monoclonal antibody mAb 13.1 following immunoprecipitation with 24–1.

C127 cells expressing CFTRΔF508 were grown for 40 hrs., at 26° C., pulsed with 360 μCi/ml $^{35}$S-methionine for 15 min. at 37° C., then chased at 37° C. or 26° C. after 4 and 5 hrs. Immunoprecipitates of cell lysates were separated on a 6% SDS-polyacrylamide gel, fluorographed with salicylate and visualized by autoradiography. The processing efficiency of CFTR in C127 cells was unaffected by temperature. In contrast, the results of these experiments show that mutant protein synthesized at 37° C. is processed normally during subsequent incubation at 26° C. but not at 37° C.

C. Effect of Temperature on cAMP-regulated Cl– Channel Current.

Whole-cell and single-channel patch-clamp studies were done as described (Rich, D. P. et al. Science 253:202–205 (1991)). For whole-cell studies the pipette (internal solution) contained 120 mM N-methyl-D-glucamine (NMDG), 5 mM HEPES, 3 mM MgCl$_2$ and 1 mM Cs EGTA (adjusted to pH 7.3 with HCl). The bath contained 140 mM NaCl, 10 mM HEPES, 1.2 mM CaSO$_4$ 1.2 mM MgSO$_4$ and 10 mM dextrose (to pH 7.3 with NaOH). When bath Cl– concentration was reduced, 120 mM sodium aspartate replaced 120 mM NaCl. For studies in excised inside-out patches, the pipette (external) solution contained: 140 mM NMDG, 2 mM MgCl$_2$, 5 mM CaCl$_2$, 100 mM L-aspartic acid, and 10 mM HEPES (to pH 7.3 with HCl) (Cl– concentration, 49 mM). The bath (internal) solution contained: 140 mM NMDG, 3 mM MgCl$_2$, 1 mM Cs EGTA, and 10 mM HEPES (to pH 7.3 with HCl) (Cl– concentration, 147 mM). All experiments were done at 35° C. Open-state probability (P$_o$) and single-channel conductance were determined from amplitude histograms. P$_o$ was measured in patches containing 5 channels. The number of channels was determined from the maximum number simultaneously open with 3 mM ATP.

3T3 fibroblasts and C127 cells expressing CFTRAUG 26, 1992F508 were cultured for 2 days at 30° C. or 37° C. One group of 3T3 fibroblasts were incubated at 30° C. for 2 days and then at 37° C. for 1 day. cAMP was increased by addition of 250 μM 8-(4-chlorophenylthio) adenosine cyclic monophosphate (CPT-cAMP) and 20 μM forskolin.

The number of cells studied in each group and the cell capacitance was 3T3 cells at 37° C. 27.2±1.2 pF (n=12); 3T3 cells at 30° C., 30.4±3.0 pF (n=10); 3T3 cells at 30° C. and then 37° C., 31.1±8.8 (n=5); C127 cells at 37° C., 27.6±2.4 (n=11); C127 cells at 30° C., 30.2±3.8 (n=10). The cAMP-stimulated current was greater in cells cultured at 30° C. than at 37° C. for both 3T3 and C127 cells (P<0.012). Current-voltage relationship of whole-cell currents under basal conditions after stimulation with cAMP agonists, and when the Cl– concentration in the bathing solution was reduced from 140 mM to 22 mM by substitution of Cl– with aspartate (low Cl–). Current-voltage relationships were obtained by a ramp voltage from –40 mV to +40 mV. Representative whole-cell currents generated by voltage steps from –100 mV to +100 mV in 50 mV increments holding voltage was –40 mV. Examples of CFTR Cl– channels in an excised, inside-out patch of membrane from 3T3 fibroblasts expressing CFTRΔF508 were obtained as follows. Cells were incubated at 30° C. for 2 days. Tracings were obtained under basal conditions, in the presence of 1 mM ATP, in the presence of 1 mM ATP plus 75 nM catalytic subunit of PKA, and after ATP and PKA were removed (wash). All traces were obtained at -100 mV. The patch contained multiple channels. All patch-clamp studies were performed at 35° C.

EXAMPLE 16

The Effect of Sodium Butyrate on Recombinant C127 Cells Expressing ΔF508 Cystic Fibrosis Transmembrane Regulator Protein A. Derivation of ΔF508-C127 Cells.

A bovine-papilloma virus based eukaryotic expression vector (pBPV-CFTR-ΔF508) containing the gene for ΔF508 CFTR and neomycin resistance were transfected into C127 cells. The C127 cells are murine mammary cells which were obtained from ATCC (#CRL 1616). The expression of the mutant ΔF508 protein and neomycin was driven using a metallothionein promoter. Following transfection, clonal cells resistant to G418 were isolated and cells expressing the mutant ΔF508 protein were subsequently identified using antibodies specific for CFTR (mAb 13.1). The cells expressing the mutant ΔF508 CFTR protein were maintained in Dulbecco's modified eagle media supplemental with glutamine and fetal calf serum.

B. Treatment of the ΔF508-C127 Cells with Butyrate and Analysis of Cells for Chloride Channel Activity.

Recombinant C127 cells expressing ΔF508 CFTR were seeded onto glass coverslips. The cells were treated with butyrate (sold as sodium butyrate by Sigma Chemical, St. Louis, Mo.) (5 mM to 50 mM concentrating in cell growth medium) twenty-four hours after seeding for eighteen to twenty-four hours. After treatment with the butyrate, the cells were analyzed for the presence of cAMP-activatable chloride channels using the 6-methoxy-N-[3-sulfopropyl]-quinolinium (SPQ) assay. The cAMP-dependent chloride activity of the mutant CFTR was assessed using the halide-sensitive fluorophore SPQ. The cells were loaded with SPQ by including 10 mM SPQ in the growth media for nine to twelve hours. The SPQ fluoresence was initially quenched by incubating the cells in a sodium iodide buffer solution (135 mM NaI, 2. 4 mM K$_2$PO$_4$; 0.6 mM KH$_2$PO$_4$; 1.0 mM MgSO$_4$; 1.0 mM CaSO$_4$; 10.0 mM HEPES pH 7.4). After measuring the fluorescence for two minutes using a Nikon inverted microscope, a Universal Imaging System and a Hamatsu camera, the sodium iodide buffer solution was replaced by a sodium nitrate buffer solution (same as the NaI solution except NaNO$_3$ was substituted for NaI). The fluorescence was measured for an additional 17.5 minutes. SPQ fluorescence is quenched by iodide but not by nitrate. The intracellular cAMP levels were increased by adding forskolin and 3-isobutyl-1-methyl-xanthene (IBMX) five minutes after the anion substitution. In this assay (hereinafter the SPQ assay) an increase in halide permeability results in SPQ fluorescence.

As shown in FIG. 15, the pretreatment of recombinant ΔF508–127 cells with butyrate resulted in the generation of cAMP-dependent chloride channel activity. Approximately 80–90% of the cells exhibited a rapid increase in fluorescence following stimulation with forskolin and IBMX (which raises intracellular levels of cAMP). These cells therefor contained functional cAMP-dependent chloride channels. This activity was absent from ΔF508-C127 cells which had not been pretreated with butyrate and mock-transfected cells. Mock transfected cells are C127 cells which had been transfected with the bovine-papilloma virus expression vector but not the ΔF508 mutant CFTR gene. These cells express the neomycin resistance gene product but not the mutant CFTR.

EXAMPLE 17

The Effect of Sodium Butyrate on Airway Epithelial Cells Derived from a Subject Having Cystic Fibrosis A. Derivation of Airway Epithelial Cells.

The human ΔF508 airway epithelial cells (DF) were derived from tissues of a CF patient homozygous for the ΔF508 mutation (gift from Dr. D. Jefferson, Tufts University, Massachusetts). The nasal epithelial cells were immortalized by SV40 Large-T antigen transduced using retroviruses. The DF cells were maintained in Dulbecco's modified eagle's media supplemented with adenine, insulin, transferrin, triodothyronine, epidermal growth factor and fetal calf serum.

B. Treatment Of the Airway Epithelial Cells with Butyrate and Analysis of the Cells for Chloride Channel Activity.

The DF cells were treated with butyrate and analyzed for chloride channel activity as described in Example 16 above. As shown in FIG. 16, the pretreatment of DF cells with butyrate resulted in the generation of cAMP-dependent chloride channel activity. Approximately 10–20% of the cells displayed a measurable increase in fluorescence following induction by forskolin and IBMX. The smaller percentage of affected cells in this example probably reflected the lower level of expression of the ΔF508 CFTR protein in these cells (10–100 fold lower). the lower amount of ΔF508 CFTR protein in these cells may be precluded detection because of the limits of the sensitivity using this system.

Those skilled in the art will now recognize or be able to ascertain using no more than routine experimentation that numerous variations and modifications of the foregoing may be made without departing from either the spirit or scope of the invention described herein. Such equivalents are intended to be encompassed within the scope of the following claims.

REFERENCES

Boat, T. Welsh, M. J., and Beaudet, A.(1989). Cystic fibrosis. In: The Metabolic Basis of Inherited Disease, C. Scriver, A. Beaudet, W. Sly, and D. Valle, eds.(McGraw Hill, New York), pp. 2649–2860.

Cheng, S. H., Harvey, R., Espino, P. C., Semba, K., Yamamoto, T., Toyoshima, K. and Smith, A. E. (1988). Peptide antibodies to the human c-fyn gene product demonstrate pp59$^{c-fyn}$ is capable of complex formation with the middle-T antigen of polyoma virus EMBO J.5, 325–334.

Cleveland, D. W., Fisher, S. G., Kirschner, M. W. and Laemmli, U.K. (1977). Peptide mapping by limited proteolysis in sodium dodecyl sulfate and analysis by gel electrophoresis. J. Biol. Chem. 252, 1102–1106.

Cohen, S. N., Chang, A. C. Y., Boyer, H. W., and Helling, R. B. (1973). Construction of biologically functional bacterial plasmids in vitro. Proc. Natl. Acad. Sci. USA 70, 3240–3244.

Cutting, G. R., Kasch, L. M., Rosenstein, B. J. Zielenski, J. Tsui, L-C., Antonarakis, S. E. and Kazanian, H. H., Jr. (1990a). A cluster of cystic fibrosis mutations in the first nucleotide binding fold of cystic fibrosis conductance regulator protein. Nature 346, 366–369.

Cutting, G. R., Kasch, L. M. Rosentein, B. J., Tsui, L.-C., Kazazian, H. H., Jr. and Antonarakis, S. E. (1990b). Two cystic fibrosis patients with mild pulmonary disease and nonsense mutations in each CFTR gene. Am. J. Hum. Genet. 47,213.

Dean, M., White, M. B., Amos, J., Gerrard, B., Stewart, C., Oskhaw, K.-T., and Leppart, M. (1990) Multiple mutations in highly conserved residues are found in mildly affected cystic fibrosis patients. Cell 61, 863–870.

Drumm, M. L., Pope, H. A., Cliff, W. H., Rommens, J. M., Marvin, S. A., Tsui, L-C., Collins, F. S., Frizzel, R. A., and Wilson, J. M. (1990) Correction of the cystic fibrosis defect in vitro by retrovirus-mediated gene transfer. Cell 62, 1227–1233.

Frizzel, R. A., Rechkemmer, G. and Shoemaker, R. L. (1986). Altered regulation of airway epithelial cell chloride channels in cystic fibrosis. Science 233, 558–560.

Gregory, R. J., Cheng, S. H., Rich, D. P., Marshall, J., Paul, S., Hehir, K., Ostedgaard, L., Klinger, K. W., Welsh, M. J., and Smith, A. E. (1990). Expression and characterization of cystic fibrosis transmembrane conductance regulator. Nature 347, 382–386.

Harlow, E., Crawford, L. V., Pim, D.C. and Williamson, N. M. (1981). Monoclonal antibodies specific for simian virus 40 tumor antigens. J. Virol. 39, 861–869.

Harper, P. S. (1989). The muscular dystrophy's. In: The Metabolic Basis of Inherited Disease, C. Scriver A. Beaudet, W. Sly and D. Valle, eds. (McGraw Hill, N.Y.), pp. 2869–2904.

Hurtley, S. M., and Helenius, A., (1989) . Protein oligomerization in the endoplasmic reticulum. Ann. Rev. Cell Biol. 5, 377–307.

Hyde,S. C, Emsley, P. Hartshorn, M. J. Mimmack, M. M. Gileadi, U., Pearce, S. R., Gallagher, M. P., Gill, D. R., Hubbard, R. E., and Higgins, C. F. (1990). Structural model of the ATP-binding proteins associated with cystic fibrosis, multidrug resistance and bacterial transport. Nature 346, 362–365.

Hwang, T.-C., Lo, L., Zeitlin, P. L., Gruenert, D. C., Huganir, R., Guggino, W. B., (1989). Cl– channels on CF: Lack of Activation by Protein Kinase C and cAMP-Dependent Protein Kinase, Science 244, 1351–1353.

Kalderon, D., Richardson, W. D., Markham, A. F. and Smith, A. E. (1985). Sequence requirements for nuclear location of simian virus 40 large-T antigen. Nature 311, 33–38.

Kerem, B.-S., Rommens, J. M., Buchanan, J. A., Markiewicz, D., Cox, T. K., Chakravarti, A., Buchwald, M., and Tsui, L.-C. (1989) Identification of the cystic fibrosis gene: genetic analysis. Science 245, 1073–1080.

Kerem, B.-S., Zielenski, J., Markiewicz, D., Bozon, D., Gazit, E., Yahaf, J., Kennedy, D., Riordan, J. R., Collins, F. S., Rommens, J. R., and Tsui, L.-C. (1990). Identification of mutations in regions corresponding to the two putative nucleotide (ATP)-binding folds of the cystic fibrosis gene. Proc. Natl. Acad. Sci. USA 87, 8447–8451.

Klausner, R. D, and Sitia, R. (1990) Protein degradation in the endoplasmic reticulum. Cell 62, 611–614. Kunkel, T. M. (1985) Rapid and efficient site-specific mutagenesis without phenotypic selection. Proc. Natl. Acad. Sci. USA 82, 488–492. Laemmli, U.K. (1970). Cleavage of structural proteins during assembly of the head of bacteriophage T4. Nature 227, 680–685.

Lehrman, M. A., Schneider, W. J., Brown, M. S., Davis, C. G., Elhammer, A., Russell, D. W., and Goldstein, J. L. (1986). The Lebanses allele at the low density lipoprotein receptor locus. Nonsense mutation produces truncated receptor that is retained in endoplasmic reticulum. J. Biol. Chem. 262, 401–410.

Li M., McCann, J. D., Liedtke, C. M., Nairn, A. C., Greengard, P. and Welsh, M. J. (1988). Cyclic AMP-dependent protein kinase opens chloride channels in normal but not cystic fibrosis airway epithelium. Nature 331, 358-360.

Li M., McCann, J. D., Anderson, M. P., Clancy, J. P., Liedtke, C. M., Nairn, A. C., Greengard, P. and Welsh, M. J. (1989). Regulation of Chloride Channels by Protein Kinase C in Normal and Cystic Fibrosis Airway Epithelia. Science 244, 1353-1356.

Lodish, H. F. (1988). Transport of secretory and membrane glycoproteins from the rough endoplasmic reticulum to the golgi. J. Biol. Chem. 263, 2107-2110. Pelham, H. R. B. (1989). Control, of protein exit from the endoplasmic reticulum. Ann. Rev. Cell Biol. 5, 1-23.

Quinton, P. M. (1989). Defective epithelial ion transport in cystic fibrosis. Clin. Chem. 35, 726-730.

Rich, D. P., Anderson, M. P., Gregory, R. J., Cheng, S. H., Paul, S., Jefferson, D. M., McCann, J. D., Klinger, K. W., Smith, A. E., and Welsh M. J. (1990) Expression of the cystic fibrosis transmembrane conductance regulator corrects defective chloride channel regulation in cystic fibrosis airway epithelial cells. Nature 347, 358-363.

Riordan, J. Rommens, J., Kerem, B.-S., Alon, N., Rozmahel, R., Grzelczack, Z., Zielenski, J., Lok, S., Plavsic, N., Chou, J.-L., Drumm, M. L., Iannuzzi, M. C., Collins, F. S., and Tsui, L.-C. (1989), Identification of the cystic fibrosis gene: cloning and characterization of the complementary DNA. Science 245, 1066-1073.

Rommens, J. H., Iannuzzi, M. C., Kerem, B.-S., Drumm, M. L., Melmer, G., Dean, M., Rozmahel, R., Cole, J. L., Kennedy, D., Hidaka, N., Zsiga, M., Buchwald, M., Riordan, J. R., Tsui, L.-C., and Collins, F. S. (1989). Identification of the cystic fibrosis gene: chromosome walking and jumping. Science 245, 1059-1065.

Rose, J. K., and Doms, R. W. (1988) Regulation of protein export from the endoplasmic reticulum. Ann. Rev. Cell. Biol. 4, 257-288.

Sambrook, J., Fritsch, E. F., and Maniatis, T. (1989). Molecular Cloning: A Laboratory Manual (Cold Spring Harbor, N.Y.: Cold Spring Harbor Laboratory).

Weatherall, D. S., Clegg, J. BB., and Wood, W. G. (1989). The hemaglobinopathies. In: The Metabolic Basis of Inherited Disease, C. Scriver, A. Beauder, W. Sly, and D. Valle, eds. (McGraw Hill, N.Y.), pp. 2281-2340.

Welsh, M. J. (1986). An apical-membrane chloride channel in human tracheal epithelium. Science 232, 1648-1650.

Welsh, M. J. and Liedtke, C. M. (1986). Chloride and Potassium Channels in Cystic Fibrosis Airway Epithelia Nature 322, 467.

TABLE 2

| Mutant | CF | Exon | CFTR Domain | A | B | C |
|---|---|---|---|---|---|---|
| Wild-type | | | | − | + | ++ |
| R334W | Y | 7 | TM6 | − | + | ++ |
| K464M | N | 9 | NBDI | − | + | − |
| Δ1507 | Y | 10 | NBDI | − | + | − |
| ΔF508 | Y | 10 | NBDI | − | + | − |
| F508R | N | 10 | NBDI | − | + | − |
| S5491 | Y | 11 | NBDI | − | + | − |
| G551D | Y | 11 | NBDI | − | + | ++ |
| N894,900Q | N | 15 | ECD4 | + | − | − |
| K1250M | N | 20 | NBD2 | − | + | ++ |
| Tth1111 | N | 22 | NBD2-Term | − | + | − |

We claim:

1. A method for treating defective chloride ion transport in a subject having cystic fibrosis said method comprising: administering to said subject an amount of an agent effective to increase the intracellular level of at least one protein in a cystic fibrosis (CF)-associated cell such that mutant cystic fibrosis transmembrane regulator protein is transported to the plasma membrane and generates chloride channels in the CF-associated cell of said subject.

2. The method of claim 1 wherein the at least one protein is a mutant cystic fibrosis transmembrane regulator protein.

3. The method of claim 1 wherein the agent is a compound having the following formula:

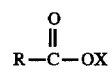

wherein R is a carboxyl moiety having from about one to about five carbon atoms selected from the group consisting of alkyls, alkenyls and alkynyls;

X is a hydrogen atom or a lower hydrocarbon group capable of being hydrolyzed under physiological conditions; and wherein said compound is provided in the form of a pharmaceutically acceptable salt.

4. The method of claim 1 wherein the CF-associated cells is an epithelial cell.

5. The method of claim 4 wherein the epithelial cell is an airway epithelial cell.

6. The method of claim 3 wherein the agent is a carboxylic acid or carboxylate.

7. The method of claim 6 wherein the carboxylate is a butyrate.

8. The method of claim 6 wherein the butyrate is sodium butyrate.

9. A packaged drug for treating defective chloride ion transport in a subject having cystic fibrosis comprising:
a container holding an agent; and
instructions for administering to said subject the agent for treating defective chloride ion transport in said subject.

10. The packaged drug of claim 9 wherein the agent is a compound having a formula as follows:

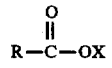

wherein R is a carboxyl moiety having from about one to about five carbon atoms selected from the group consisting of alkyls, alkenyls and alkynyls;

X is a hydrogen atom or a lower hydrocarbon group capable of being hydrolyzed under physiological conditions; and wherein said compound is provided in the form of a pharmaceutically acceptable salt.

11. The packaged drug of claim 10 wherein the agent is a carboxylic acid or carboxylate.

12. The packaged drug of claim 11 wherein the carboxylate is a butyrate.

13. The packaged drug of claim 12 wherein the butyrate is sodium butyrate.

14. The method of claim 3 wherein the lower hydrocarbon group esterifies the carboxyl group and is selected from the group consisting of methyl, ethyl and propyl.

15. The method of claim 3 wherein the pharmaceutically acceptable salt is selected from the group consisting of sodium, potassium and hemisulfate.

16. The method of claim 6 wherein the carboxylic acid is butyric acid.

17. The packaged drug of claim 10 wherein the lower hydrocarbon group esterifies the carboxyl group and is selected from the group consisting of methyl, ethyl and propyl.

18. The packaged drug of claim 10 wherein the pharmaceutically acceptable salt is selected from the group consisting of sodium, potassium and hemisulfate.

19. The packaged drug of claim 9 wherein the carboxylic acid is butyric acid.

20. A method for generating chloride channels in a cystic fibrosis (CF)-associated cell, the method comprising:
contacting said cell with an amount of an agent effective to increase the intracellular level of at least one protein in said cell such that mutant cystic fibrosis transmembrane regulator protein is transported to the plasma membrane of said cell and generates chloride channels therein.

21. The method of claim 20 wherein the at least one protein is a mutant cystic fibrosis transmembrane regulator protein.

22. The method of claim 20 wherein the CF-associated cell is an epithelial cell.

23. The method of claim 22 wherein the epithelial cell is an airway epithelial cell.

24. The method of claim 20 wherein the agent is a compound having the following formula:

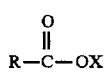

wherein R is a carboxyl moiety having from about one to about five carbon atoms selected from the group consisting of alkyls, alkenyls and alkynyls;

X is a hydrogen atom or a lower hydrocarbon group capable of being hydrolyzed under physiological conditions; and wherein said compound is provided in the form of a pharmaceutically acceptable salt.

25. The method of claim 24 wherein the lower hydrocarbon esterifies the carboxyl group and is selected from the group consisting of methyl, ethyl and propyl.

26. The method of claim 24 wherein the pharmaceutically acceptable salt is selected from the group consisting of sodium, potassium and hemisulfate.

27. The method of claim 24 wherein the agent is a carboxylic acid or carboxylate.

28. The method of claim 27 wherein the carboxylic acid is butyric acid.

29. The method of claim 27 wherein the carboxylate is a butyrate.

30. The method of claim 29 wherein the butyrate is sodium butyrate.

31. A method for generating chloride channels in a cystic fibrosis (CF)-associated cell, the method comprising increasing the intracellular level of at least one protein in said cell such that mutant cystic fibrosis transmembrane regulator protein is transported to the plasma membrane of said cell and generates chloride channels therein.

32. The method of claim 31 wherein the at least one protein is a mutant cystic fibrosis transmembrane regulator protein.

33. The method of claim 31 wherein the CF-associated cell is an epithelial cell.

34. The method of claim 33 wherein the epithelial cell is an airway epithelial cell.

* * * * *